United States Patent

Batt et al.

[11] Patent Number: 5,932,586
[45] Date of Patent: *Aug. 3, 1999

[54] PROSTAGLANDIN SYNTHASE INHIBITORS

[75] Inventors: Douglas Guy Batt, Wilmington; Donald Joseph Phillip Pinto, Newark; Michael James Orwat, Wilmington, all of Del.; Joseph James Petraitis, Glenmoore, Pa.; William John Pitts, Newark, Del.

[73] Assignee: DuPont Pharmaceuticals Company, Wilmington, Del.

[*] Notice: This patent is subject to a terminal disclaimer.

[21] Appl. No.: 08/753,029

[22] Filed: Nov. 19, 1996

Related U.S. Application Data

[62] Division of application No. 08/314,991, Sep. 29, 1994, Pat. No. 5,593,994.

[51] Int. Cl.⁶ ..................................... A01N 43/58
[52] U.S. Cl. ........................... 514/277; 546/339; 560/11; 560/27; 558/61; 568/28; 568/67; 564/162; 514/252
[58] Field of Search ..................... 514/277, 252; 546/339; 560/11; 558/61; 568/28, 67; 564/162

[56] References Cited

U.S. PATENT DOCUMENTS 2,961,318  11/1960  Jones .
3,624,142  11/1971  Shen et al. .
4,613,611  9/1986  Floyd, Jr. et al. .

FOREIGN PATENT DOCUMENTS 130045  1/1985  European Pat. Off. .

OTHER PUBLICATIONS

Newkome et al J. Org. Chem 1980, 45:4380.
Bushby et al J. Chem Soc. Perkin Trans I 1986 721.
Hori et al Chem. Pharm. Bull 1974 22:2020.
Tilley et al J. Med. Chem 1989 32:1814.

*Primary Examiner*—Paul J. Killos
*Attorney, Agent, or Firm*—Karen H. Kondrad

[57] ABSTRACT

This invention relates to ortho substituted phenyl compounds as inhibitors of prostaglandin synthase, to pharmaceutical compositions comprising such compounds and to methods of using such compounds as antiinflammatory and antipyretic agents. The class of compounds useful in this method of treatment is represented by Formula I below:

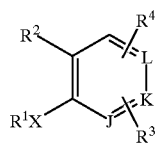

(I)

9 Claims, No Drawings

PROSTAGLANDIN SYNTHASE INHIBITORS

This is a division of application Ser. No. 08/314,991 filed Sep. 29, 1994, now U.S. Pat. No. 5,593,994. The disclosure of this earlier filed application is hereby incorporated by reference.

FIELD OF THE INVENTION

This invention relates to ortho substituted phenyl compounds as inhibitors of prostaglandin synthase, to pharmaceutical compositions comprising such compounds and to methods of using such compounds as antinflammatory and antipyretic agents.

BACKGROUND OF THE INVENTION

Nonsteroidal antuinflammatory drugs (NSAID's) have been the mainstay of antirheumatic and antunflammatory drug therapy for over 200 years (Weissman, G., Scientific American 84–90, 1991). NSAID's function through inhibition of prostaglandin biosynthesis (Vane, J. R., Nature-New Biology 231, 232–235, 1971). Specifically, these agents act as cyclooxygenase (prostaglandin G/H synthase) inhibitors. Cyclooxygenase is the first enzyme in the arachidonic acid cascade, leading to prostaglandins of the $D_2$, $E_2$, and $F_{2a}$ series. In addition, prostacyclin ($PGI_2$) and thromboxanes $A_2$ and $B_2$ are derived from a cyclooxygenase-generated $PGHS_2$ intermediate (Prostaglandins and Related Substances—A Practical Approach (1987). Benedetto, C., McDonald-Gibson, R. G., and Nigam, S., and Slater, T. F., eds. IRL Press, Washington, D.C). These arachidonic acid metabolites are involved in the processes of pain, fever, blood clotting and inflammation. In addition, prostaglandins are responsible for maintaining gastrointestinal mucosal integrity (Cryer, B., and Feldman, M., Arch Intern. Med. 152, 1145–1155, 1992) and renal function, particularly under conditions of stress (Whelton, A., and Hamilton, C. W., J. Clin. Pharmacol. 31, 588–598, 1994). Thus, agents which inhibit the cyclooxygenase enzyme have beneficial antiinflammatory and analgesic properties due to blockade of inflammatory and pain-mediator production, but by virtue of their mechanism of action, these same agents have liabilities associated with gastrointestinal and renal function. Minimizing or eliminating these-liabilities in a new therapy provides the rationale for searching for a "safe" NSAID with an improved GI and renal profile (Vane, J. R., Nature 367, 215–216, 1994).

Until recently, it had been assumed that only one cyclooxygenase isozyme was responsible for all prostaglandin G/H2 synthase activity. However, a newly identified, mitogen-inducible form of this enzyme, termed cyclooxygenase 2 (Cox 2), has been described (Xie, W., Chipman, J. G., Robertson, D. L., Erickson, R. L., and Simmons, D. L., Proc. Natl. Acad. Sci. 88, 2692–2696, 1991; Kujubu, D. A., Fletcher, B. S., Varnum, B. C., Lim, R. W., and Herschman, H. R., J. Biol Chem. 266(20) 12866–12872, 1991; Hla, T., and Neilson, K., Proc. Natl. Acad. Sci. 89, 7384–7388, 1991; Xie, W., Robertson, D. L., and Simmons, D. L., Drug Development Research 25, 249–265, 1992). Cox 2 displays physical and biological properties distinct from the classic cyclooxygenase species, Cox 1. The tissue and cellular distribution of Cox 2, along with its regulated expression, implicate its involvement in inflammatory responses and disease states such as rheumatoid arthritis, while Cox 1 expression is responsible for constitutive functions. Based upon the distinction between Cox 1 and Cox 2, the previous hypotheses explaining NSAID effects, which rely on a single isozyme, must be questioned. Specifically, the antiinflammatory and analgesic action of NSAID's attributed exclusively to inhibition of the constitutive Cox 1 isozyme cannot be accepted. In fact, a more probable hypothesis is that the antiinflammatory and analgesic action of most NSAID's in response to a chronic stimulus can be accounted for by inhibition of the inducible Cox 2 species, while GI and renal liabilities of existing NSAID's are due to inhibition of the constitutively expressed Cox 1 enzyme (Vane, J. R., Nature 367, 215–216, 1994). Thus, agents which possess selective or specific inhibition of Cox 2 can be expected to provide improved GI and renal safety while maintaining a high degree of antiinflammatory, antipyretic and analgesic activity.

The potential for a safer NSAID through selective inhibition has prompted evaluation of compounds on purified enzyme preparations. Preferential inhibition of either isoenzyme or equal inhibitory potency has been obtained with a collection of therapeutically useful NSAIDS (DeWitt, D. L., Meade, E. A., and Smith, W. L., Amer. J. Med. 95 (Suppl. 2A), 40S–44S, 1993). Only one compound in this collection, however, displayed Cox 2 selectivity, namely 6-methoxy naphthylacetic acid (6MNA), the nebumetone active metabolite. Several other agents with similar Cox-2 selectivity have also been described including BF389 (Mitchell, J. A., Akarasereenot, P., Thiemermann, C., Flower, R. J., and Vane, J. R., Proc. Natl. Acad. Sci. 90, 11693–11697, 1994) and NS-398 (Futaki, N., Takahashi, S., Yokayama, M., Arai, I., Higuchi, S., and Otomo, S., Prostaglandins 47, 55–59, 1994; Masferrer, J. L., Zuieifel, B. S., Manning, P. T., Hauser, S. D., Leaky, K. M., Smith, W. G., Isakson, P. C., and Seibert, K., Proc. Natl. Acad. Sci. 91, 3228–3232, 1994). With the latter compound, selective inhibition of Cox-2 blocked proinflammatory prostaglandin synthesis in vivo in response to carrageenan, but did not block gastric prostaglandin synthesis nor produce gastic lesions (Masferrer et al, vide supra).

The findings support the premise that selective Cox-2 inhibitors will possess potent antiiflammatory properties and improved safety profile. Detailed mechanistic studies have revealed that NS-398 along with a second Cox-2 selective inhibitor, DuP 697, achieve their selectivity through a unique process (Copeland, R. A., Williams, J. M., Giannaras, J., Nurnberg, S., Covington, M., Pinto, D., Pick, S., and Trzaskos, J. M. Mechanism of Selective Inhibition of the Inducible Isoform of Prostaglandin G/H Synthase. Submitted). The inhibition is competitive toward both isoenzymes, but displays selective time-dependence against Cox-2 resulting in enhanced inhibition with longer exposure. Time-dependence produces an extremely tight binding inhibition which can only be reversed following enzyme denaturation and organic extraction.

Newkome G. R. et. al. (J. Org. Chem. 1980, 45, 4380) report bis-(5-carboxy-2-pyridyl)benzenes, but no utility for these compounds is disclosed.

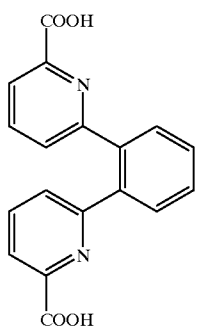

Bushby et. al. (J. Chem. Soc. Perkin Trans. I 721, 1986) describe the synthesis of substituted terphenyls including the example shown below.

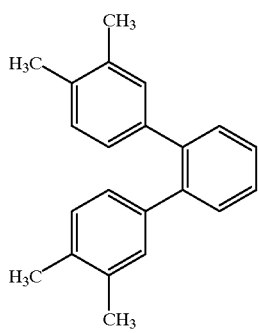

Hori M. et. al. (Chem. Pharm. Bull. 22(9), 2020, 1974,) report the synthesis of terphenyls, including 2-phenyl-2'-methylthio-1-biphenyl.

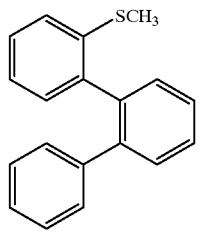

Kemp et. al. (J. Org. Chem. 46, 5441, 1981), report the synthesis of 4-methoxyphenyl-(4'-alkylphenyl) benzenes.

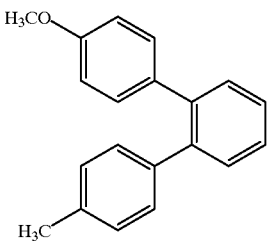

Floyd et. al., U.S. Pat. No. 4,613,611 disclose a-hydroxy-b-oxo-[1,1':2',1''-terphenyl]-4-ethanesulfonic acid, monosodium salt for the treatment of Diabetes Mellitus.

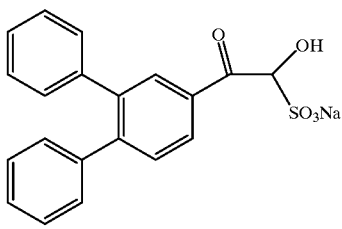

Ortho-bis(dimethoxyphenyl)benzene carboxamides have been reported (Tilley, et. al. J. Med. Chem. 32, 1814, 1989) as platelet-activating factor antagonists.

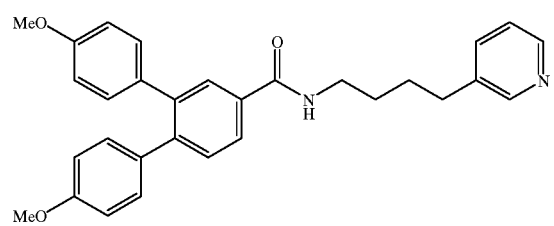

European Patent Application EP130045 A1, published Jan. 2, 1985 discloses substituted bis-(methoxyphenyl) benzenes as analgesic and antiinflammatory agents.

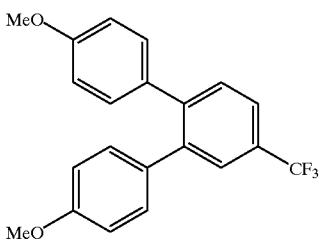

U.S. Pat. No. 3,624,142 discloses 4-methylsulfonyl-biphenylacetic acids as antiflammatory agents.

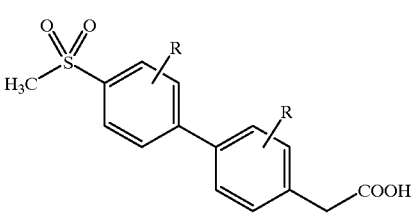

None of the above references teach or suggest the methylsulfonyl compounds of the present invention. Thus, it is the object of the present invention to provide compounds which are prostaglandin synthase inhibitors, including compounds which are selective Cox 2 inhibitors, as novel antiinflammatory agents with an improved therapeutic profile for use in rheumatic and inflammatory diseases and in the treatment of pyresis.

SUMMARY OF THE INVENTION

This invention relates to ortho substituted phenyls of Formula I described below as inhibitors of prostaglandin synthase, to pharmaceutical compositions comprising such compounds and to methods of using such compounds as antiinflammatory and antipyretic agents.

DETAILED DESCRIPTION OF THE INVENTION

There is provided by this invention a compound of Formula I:

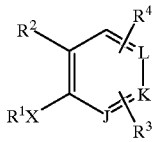

(I)

or a pharmaceutically acceptable salt or prodrug form thereof, wherein:

J, K, and L are independently $CR^3$, $CR^4$ or N;

X is a single bond, (i.e. X is absent), $-(CHR^5)_2-$, $-CH=CR^5-$, $-CR^5=CH-$, $-C\!\!\int\!\! C-$, $-(CHR^5)_pZ-$, $-Z(CHR^5)_p-$, $-C(=O)CH_2$, or $-CH_2C(=O)-$;

Z is O or S;

$R^1$ is:
- phenyl substituted with 0–2 $R^7$,
- 2-naphthyl substituted with 0–2 $R^7$,
- $C_5-C_7$ cycloalkyl substituted with 0–1 $R^9$,
- $C_5-C_7$ cycloalkenyl, provided that when $R^1$ is attached directly to a heteroatom, said heteroatom is not attached to a carbon bearing a double bond in the cycloalkene ring,.
- a 5- to 10-membered heterocyclic ring system selected from furyl, thienyl, pyrrolyl, thiazolyl, oxazolyl, N-methylpyrrolyl, isoxazolyl, isothiazolyl, pyrazolyl, 3-pyridinyl, pyrazinyl, benzofuranyl, benzothienyl, benzothiazolyl, benzoxazolyl, benzotriazolyl, benzoisothiazolyl, benzisoxazolyl, quinolinyl, isoquinolinyl, or piperidinyl, said heterocyclic ring system being substituted with 0–2 $R^7$;

$R^2$ is:

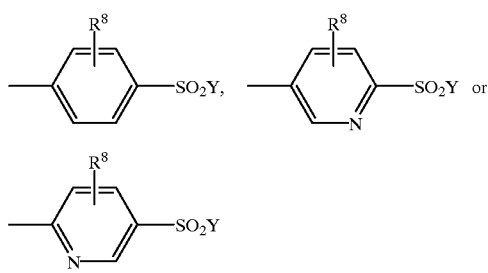

Y is $-CH_3$ or $NH_2$;

$R^3$ is: H, F, Br, Cl, I, CN, $C_1-C_4$ alkyl substituted with 0–1 $R^{12}$, $C_1-C_4$ haloalkyl, $C_1-C_4$ alkenyl substituted with 0–1 $R^{13}$, $NO_2$, $NR^{15}R^{16}$, $S(O)_mR^{11}$, $SO_2NR^{15a}R^{16}$, $-C(=O)R^6$, $-COOR^{17}$, $-C(O)NR^{15a}R^{16}$, or $OR^{18}$;

$R^4$ is H, F, Br, Cl, I, $C_1-C_2$ alkyl, $C_1-C_2$ alkoxy, $C_1-C_2$ haloalkyl, $-CH_3$, $-SR_{10a}$;

Alternately, when $R^3$ and $R^4$ are substituents on adjacent carbon atoms, $R^3$ and $R^4$ can be taken together with the carbon atoms to which they are attached to form a 5–7 membered carbocyclic or heterocyclic ring system, said heterocyclic ring system containing from 1–3 heteroatoms selected from N, O or S;

$R^5$ is $C_1-C_2$ alkyl, $C_1-C_2$ alkoxy, or $C_1-C_2$ haloalkyl;

$R^6$ is
- hydrogen,
- $C_1-C_6$ alkyl substituted with 0–1 $R^{14}$,
- phenyl substituted with 0–2 $R^9$,
- $C_5-C_7$ cycloalkyl substituted with 0–1 $R^9$,
- a 5- to 10-membered heterocyclic ring system selected from furyl, thienyl, thiazolyl, oxazolyl, N-methylpyrrolyl, isoxazolyl, isothiazolyl, pyrazolyl, pyridinyl, pyridazinyl, pyrazinyl, or pyrimidinyl, said heterocyclic ring system being substituted with 0–2 $R^7$;

$R^7$ is a substituent on carbon that is selected from: H, F, Br, Cl, I, $C_1-C_4$ alkyl, phenyl, $CH_2OH$, $CH_2OCH_3$, $C_1-C_4$ alkoxy, $C_1-C_4$ haloalkyl, $-SR^{10}$, $NR^{15}R^{16}$, $-C(=O)R^{10a}$, $CH_2COOR^{17}$, or $OR^{19}$; provided that when X is a single bond then $R^7$ is not ortho to X.

$R^8$ is H, F, Br, Cl, I, $C_1-C_4$ alkyl, $C_1-C_4$ alkoxy;

$R^9$ is H, F, Br, Cl, I, hydroxy, $C_1-C_4$ alkyl, or $C_1-C_4$ alkoxy;

$R^{10}$ is H or $C_1-C_4$ alkyl;

$R^{10a}$ is $C_1-C_4$ alkyl;

$R^{11}$ is $C_1-C_4$ alkyl, $C_1-C_2$ fluoroalkyl, phenyl, or benzyl;

$R^{12}$ is F, $OR^{18}$, $NR^{15}R^{16}$, phenyl substituted with 0–2 $R^9$, $-CN$, $-C(=O)R^6$, $-COOR^{17}$, $-C(=O)NR^{15}R^{16}$, or
- a heterocyclic ring system selected from morpholinyl, piperidinyl, pyrrolidinyl, furyl, thienyl, pyridinyl, piperidazinyl, pyrimidinyl, pyrazinyl, or tetrahydropyridinyl, said heterocyclic ring system being substituted with 0–2 $R^9$;

$R^{13}$ is $-CN$, $-C(=O)R^6$, $-COOR^{17}$, $-NO_2$, or $NR^{15}R^{16}$;

$R^{14}$ is F, OH, $C_1-C_4$ alkoxy, $NH_2$, phenyl substituted with 0–2 $R^9$, alkylcarbonyl, arylcarbonyl, $-COOR^{17}$, or $-C(=O)NH_2$;

$R^{15}$ is H, $C_1-C_4$ alkyl substituted with 0–1 $R^{23}$, $C_6-C_{10}$ aryl, $C_3-C_7$ cycloalkyl, $C_4-C_{11}$ cycloalkylalkyl, $C_2-C_4$ alkenyl, $C_1-C_4$ alkoxy, $C_1-C_6$ alkylcarbonyl, $C_1-C_6$ alkoxycarbonyl, $C_7-C_{14}$ arylalkoxycarbonyl, $C_6-C_{10}$ aryloxycarbonyl, $C_1-C_6$ alkylaminocarbonyl, $C_6-C_{10}$ arylcarbonyl, $C_1-C_6$ alkylsulfonyl, $C_6-C_{10}$ arylsulfonyl, $C_7-C_{14}$ alkylarylsulfonyl, or $C_7-C_{14}$ arylalkylsulfonyl;

$R^{15a}$ is H, $C_1-C_4$ alkyl substituted with 0–1 $R^{23}$, $C_6-C_{10}$ aryl, $C_3-C_7$ cycloalkyl, $C_4-C_{11}$ cycloalkylalkyl, $C_2-C_4$ alkenyl, or $C_1-C_4$ alkoxy;

$R^{16}$ is H, or $C_1-C_4$ alkyl; or

Alternately, $R^{15}$ and $R^{16}$ can be taken together to be $-(CH_2)_4-$, $-(CH_2)_5-$, $-(CH_2)_2O(CH_2)_2-$, or $-(CH_2)_2NR^{21}(CH_2)_2-$, $R^{17}$ is 01–04 alkyl, or arylalkyl; $R^{18}$ is 01–04 alkyl substituted with 0–2 $R^{24}$, $C_6-C_{10}$ aryl, $C_3-C_7$ cycloalkyl, $C_1-C_6$ alkylcarbonyl, $C_1-C_6$ alkylaminocarbonyl, $C_7-C_{14}$ arylalkylcarbonyl, or C6-C10 arylcarbonyl substituted with 0–2 $R^9$;

$R^{19}$ is $C_1-C_4$ alkyl, $C_1-C_4$ haloalkyl, $C_1-C_4$ alkoxyalkyl, $C_1-C_6$ alkylcarbonyl, $C_1-C_6$ alkylaminocarbonyl, $C_7-C_{14}$ arylalkylcarbonyl, or $C_6-C_{10}$ arylcarbonyl substituted with 0–2 $R^9$;

$R^{20}$ is $C_1-C_4$ alkyl, $C_1-C_4$ haloalkyl, $C_1-C_4$ alkoxyalkyl, $C_6-C_{10}$ aryl, $C_3-C_7$ cycloalkyl, $C_1-C_6$ alkylcarbonyl, $C_1-C_6$ alkylaminocarbonyl, $C_7-C_{14}$ arylalkylcarbonyl, or $C_6-C_{10}$ arylcarbonyl substituted with 0–2 $R^9$;

$R^{21}$ is $C_1-C_4$ alkyl or benzyl;

$R^{22}$ is H, $R^2$, $R^1$, $C_1$–$C_4$ alkyl, $C_4$–$C_{10}$ cycloalkylalkyl, $C_7$–$C_{14}$ arylalkyl, or $C_6$–$C_{10}$ heteroarylalkyl;

$R^{23}$ is H, F, phenyl substituted with 0–2 $R^9$, —C(=O)$R^6$, —COOR$^{17}$, —C(=O) NHR$^{16}$, or a heterocyclic ring system selected from morpholinyl, piperidinyl, pyrrolidinyl, furyl, thienyl, or tetrahydropyridinyl, said heterocyclic ring system being substituted with 0–2 $R^9$;

$R^{24}$ is:

H, F, NR$^{15}$R$^{16}$, phenyl substituted with 0–2 $R^9$, $C_1$–$C_4$ alkoxy, $C_1$–$C_4$ alkylcarbonyloxy, C(=O)$R^6$, —COOR$^{17}$, —C(=O) NR$^{15}$R$^{16}$, or a heterocyclic ring system selected from morpholinyl, piperidinyl, pyrrolidinyl, furyl, thienyl, or tetrahydropyridinyl, said heterocyclic ring system being substituted with 0–2 $R^9$;

m is 0–2; and p is 0–1.

provided that:

when J and L are both nitrogen and K is CR$^4$, then $R^4$ cannot be SR$^{10}$;

when $R^3$ and $R^4$ are taken together to form a 6 membered carbocyclic ring system and $R^1$X is phenyl, $R^2$ is not 4-methylsulfonylphenyl;

when J is nitrogen and $R^3$ and $R^4$ are hydrogen and $R^1$X is phenyl, $R^2$ is not 4-methylsulfonylphenyl;

when $R^3$ and $R^4$ are hydrogen and $R^1$X is phenyl, $R^2$ is not 4-aminosulfonylphenyl.

Preferred are compounds of Formula I or pharmaceutically acceptable salts or prodrugs thereof, wherein:

J is CH or N;

Each of K and L independently is CR$^3$ or CR$^4$;

X is a single bond, (i.e. X is absent), —C∫C—, or —(CHR$^5$)$_p$Z—;

$R^3$ is: H, F, Br, CN, $C_1$–$C_4$ alkyl substituted with 0–1 $R^{12}$, $C_1$–$C_4$ haloalkyl, NO$_2$, SO$_m$R$^{11}$, —C(=O)$R^6$, or OR$^{18}$;

$R^4$ is H, F, CH$_3$, or

Alternately, when $R^3$ and $R^4$ are substituents on adjacent carbon atoms, $R^3$ and $R^4$ can be taken together with the carbon atoms to which they are attached to form a 5–7 membered carbocyclic ring system;

$R^6$ is hydrogen, $C_1$–$C_6$ alkyl substituted with 0–1 $R^{14}$, or phenyl substituted with 0–2 $R^9$;

$R^7$ is a substituent on carbon that is selected from: H, F, Br, $C_1$–$C_4$ alkyl, CH$_2$OH, CH$_2$OCH$_3$, $C_1$–$C_4$ alkoxy, $C_1$–$C_4$ haloalkyl, NR$^{15}$R$^{16}$, or —C(=O)$R^{10}$; and where all other substituents for Formula I are as defined herein above, provided that:

when $R^3$ and $R^4$ are taken together to form a 6 membered carbocyclic ring system and $R^1$X is phenyl, $R^2$ is not 4-methylsulfonylphenyl;

when J is nitrogen and $R^3$ and $R^4$ are hydrogen and $R^1$X is phenyl, $R^2$ is not 4-methylsulfonylphenyl;

when $R^3$ and $R^4$ are hydrogen and $R^1$X is phenyl, $R^2$ is not 4-aminosulfonylphenyl.

Further preferred are the preferred compounds of Formula I, or pharmaceutically acceptable salts or prodrugs thereof, wherein:

$R^8$ is H;

$R^9$ is H;

$R^{12}$ is F, OR$^{18}$, CN, —COOR$^{17}$;

$R^{14}$ is H;

$R^{15}$ is H, or $C_1$–$C_4$ alkyl;

$R^{16}$ is H or $C_1$–$C_4$ alkyl;

$R^{18}$ is H or $C_1$–$C_4$ alkyl;

$R^{19}$ is $C_1$–$C_4$ alkyl.

provided that:

when $R^3$ and $R^4$ are taken together to form a 6 membered carbocyclic ring system and $R^1$X is phenyl, $R^2$ is not 4-methylsulfonylphenyl;

when J is nitrogen and $R^3$ and $R^4$ are hydrogen and $R^1$X is phenyl, $R^2$ is not 4-methylsulfonylphenyl;

when $R^3$ and $R^4$ are hydrogen and $R^1$X is phenyl, $R^2$ is not 4-aminosulfonylphenyl.

Further preferred are compounds of Formula Ia or pharmaceutically acceptable salts or prodrugs, thereof, selected from the group thereof wherein:

(a) compounds of Formula Ia:

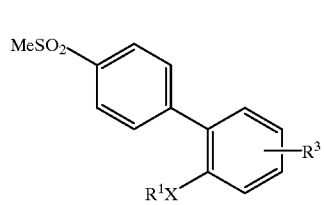

(Ia)

wherein:

$R^1$X is phenyl, 4-fluorophenyl, 3-methoxyphenyl, 4-methoxyphenyl, 3,4-dimethoxyphenyl, 4-hydroxymethylphenyl, 4-methoxymethylphenyl, 4-dimethylaminophenyl, 4-formylphenyl, 2-naphthyl, 5-methoxy-2-naphthyl, 2-quinolinyl, 3-quinolinyl, 2-benzothienyl, 5-benzothienyl, 3-pyridyl, phenylacetylenyl, phenoxy, cyclohexenyl, cyclohexyl, 4-fluorophenoxy, cyclohexyloxy, benzyloxy, 1-pyrrolyl or 1-piperidinyl; and $R^3$ is hydrogen, 4-hydroxy, 4-nitro, 5-nitro or 4-aceto.

More preferred are compounds of Formula Ia or pharmaceutically acceptable salts or prodrugs, thereof, selected from the group thereof wherein:

$R^1$X is phenyl; and $R^3$ is hydrogen, 4-hydroxy, 4-nitro, 5-nitro or 4-aceto; or $R^1$X is 4-fluorophenyl, 3-methoxyphenyl, 4-methoxyphenyl, 3,4-dimethoxyphenyl, 4-hydroxymethylphenyl, 4-methoxymethylphenyl, 4-dimethylaminophenyl, 4-formylphenyl, 2-naphthyl, 5-methoxy-2-naphthyl, 2-quinolinyl, 3-quinolinyl, 2-benzothienyl, 5-benzothienyl, 3-pyridyl, phenylacetylenyl, phenoxy, cyclohexenyl, cyclohexyl, 4-fluorophenoxy, cyclohexyloxy, benzyloxy, 1-pyrrolyl or 1-piperdinyl; and $R^3$ is hydrogen.

Specifically preferred are compounds from the group consisting of:

(a) 2-(4'-methylsulfonylphenyl)-1-biphenyl, (b) 2-(4'-methylsulfonylphenyl)-1-(4'-flourophenyl)-benzene, (c) 2-(4'-methylsulfonylphenyl)-1-(4'-methylphenyl)-benzene, (d) 2-(4'-methylsulfonylphenyl)-1-(3'-methoxyphenyl)
(e) 2-(4'-methylsulfonylphenyl)-1-(4'-methoxyphenyl)-benzene,
(f) 2-(4'-methylsulfonylphenyl)-1-(3',4'-methoxyphenyl)-benzene,
(g) 2-(4'-methylsulfonylphenyl)-1-(4'-aminophenyl)-benzene,
(h) 2-(4'-methylsulfonylphenyl)-1-(4'-dimethylaminophenyl)-benzene,
(i) 2-(4'-methylsulfonylphenyl)-1-(4'-benzaldehyde)-benzene,
(j) 2-(4'-methylsulfonylphenyl)-1-(4'-methoxymethylphenyl)-benzene,
(k) 2-(4'-methylsulfonylphenyl)-1-(4'-hydroxymethylphenyl)-benzene,
(l) 2-(4'-methylsulfonylphenyl)-1-(5-benzothienyl)-benzene,
(m) 2-(4'-methylsulfonylphenyl)-1-(2-benzothienyl)-benzene,
(n) 2-(4'-methylsulfonylphenyl)-1-(2-naphthyl)-benzene,
(o) 2-(4'-methylsulfonylphenyl)-1-(5'-methoxy-2-naphthyl)-benzene,
(p) 2-(4'-methylsulfonylphenyl)-1-(3-pyridyl)-benzene,
(q) 2-(4'-methylsulfonylphenyl)-1-(2-quinolyl)-benzene,
(r) 2-(4'-methylsulfonylphenyl)-1-(3-quinolyl)-benzene,
(s) 2-(4'-methylsulfonylphenyl)-1-(cyclohexenyl)-benzene,
(t) 2-(4'-methylsulfonylphenyl)-1-(cyclohexyl)-benzene,
(u) 2-(4'-methylsulfonylphenyl)-1-(4'-fluorophenyl)-(4'-amino)-benzene,
(v) 2-(4'-methylsulfonylphenyl)-1-(4'-fluorophenyl)-(5'-amino)-benzene,
(w) 2-(4'-methylsulfonylphenyl)-1-(4'-fluorophenyl)-(4'-nitro)-benzene,
(x) 2-(4'-methylsulfonylphenyl)-1-(4'-fluorophenyl)-(5'-nitro)-benzene,
(y) 2-(4'-methylsulfonylphenyl)-1-(4'-fluorophenyl)-(4'-trifluromethyl)-benzene,
(z) 2-(4'-methylsulfonylphenyl)-1-(4'-fluorophenyl)-4-bromobenzene,
(aa) 2-(4'-methylsulfonylphenyl)-1-(4'-fluorophenyl)-4-chlorobenzene,
(bb) 2-(4'-methylsulfonylphenyl)-1-(4'-fluorophenyl)-4-acetylbenzene,
(cc) 2-(4'-methylsulfonylphenyl)-1-(4'-fluorophenoxy)-benzene,
(dd) 2-(4'-methylsulfonylphenyl)-1-(cyclohexyloxy)-benzene,
(ee) 2-(4'-methylsulfonylphenyl)-1-(phenoxy)-benzene,
(ff) 2-(4'-methylsulfonylphenyl)-1-(benzyloxy)-benzene,
(gg) 2-(4'-methylsulfonylphenyl)-1-(piperidinyl)-benzene,
(hh) 2-(4'-methylsulfonylphenyl)-1-(phenylacetylene)-benzene,
(ii) 2-(4'-methylsulfonylphenyl)-1-(pyrrolyl)-benzene,
(jj) 2-(5-methylsulfonyl-2-pyridyl)-1-(4'-methylphenyl)-benzene,
(kk) 2-(5-methylsulfonyl-2-pyridyl)-1-(4'-fluorophenyl)-benzene,
(ll) 2-(2-methylsulfonyl-2-pyridyl)-1-biphenyl,
(mm) 3-(4'-methylsulfonylphenyl)-2-(4'-fluorophenyl)-pyridine
(nn) 3-(4'-methylsulfonylphenyl)-2-(4'-methoxyphenyl)-pyridine
(oo) 3-(4'-methylsulfonylphenyl)-2-(4'-methylphenyl)-pyridine The present invention also provides pharmaceutical compositions comprising a compound of Formula I and a pharmaceutically acceptable carrier.

The compounds described above are useful as antiinflammatory and antipyretic agents in a mammal when administered as pharmaceutical compositions to a mammal in need of treatment with such antiinflammatory or antipyretic agents. The present invention includes pharmaceutical compositions containing an effective PGHS-2-inhibiting or antiinflammatory or antipyretic amount of the above described compounds of Formula I. The present invention also includes methods of treating arthritis and other inflammatory diseases in a mammal comprising administering to the mammal a therapeutically effective amount of a compound of Formula I described above.

The compounds of the present invention can also be administered in combination with one or more additional therapeutic agents. Administration of the compounds of Formula I of the invention in combination with such additional therapeutic agent, may afford an efficacy advantage over the compounds and agents alone, and may do so while permitting the use of lower doses of each. A lower dosage minimizes the potential of side effects, thereby providing an increased margin of safety.

By "therapeutically effective amount" it is meant an amount of a compound of Formula I that when administered alone or in combination with an additional therapeutic agent to a cell or mammal is effective to inhibit PGHS-2 so as to prevent or ameliorate the inflammatory disease condition or the progression of the disease.

By "administered in combination" or "combination therapy" it is meant that the compound of Formula I and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

The compounds herein described may have asymmetric centers. Unless otherwise indicated, all chiral, diastereomeric and racemic forms are included in the present invention. Many geometric isomers of olefins, C=N double bonds, and the like can also be present in the compounds described herein, and all such stable isomers are contemplated in the present invention. It will be appreciated that compounds of the present invention may contain asymmetrically substituted carbon atoms, and may be isolated in optically active or racemic forms. It is well known in the art how to prepare optically active forms, such as by resolution of racemic forms or by synthesis, from optically active starting materials. All chiral, diastereomeric, racemic forms and all geometric isomeric forms of a structure are intended, unless the specific stereochemistry or isomer form is specifically indicated.

When any variable occurs more than one time in any constituent or in any Formula, its definition on each occurrence is independent of its definition at every other occurrence. Thus, for example, if a group is shown to be substituted with 0–3 $R^6$, then said group may optionally be substituted with up to three $R^6$ and $R^6$ at each occurrence is selected independently from the defined list of possible $R^6$. Also, by way of example, for the group —N($R^{5a}$)$_2$, each of the two $R^{5a}$ substituents on N is independently selected from the defined list of possible $R^{5a}$. Similarly, by way of example, for the group $-C(R^7)_2-$, each of the two $R^7$ substituents on C is independently selected from the defined list of possible $R^7$.

When a bond to a substituent is shown to cross the bond connecting two atoms in a ring, then such substituent may be bonded to any atom on the ring.

When a substituent is listed without indicating the atom via which such substituent is bonded to the rest of the compound of Formula I, then such substituent may be bonded via any atom in such substituent. For example, when the substituent is piperazinyl, piperidinyl, or tetrazolyl, unless specified otherwise, said piperazinyl, piperidinyl, tetrazolyl group may be bonded to the rest of the compound of Formula I via any atom in such piperazinyl, piperidinyl, tetrazolyl group.

Combinations of substituents and/or variables are permissible only if such combinations result in stable compounds. By stable compound or stable structure it is meant herein a compound that is sufficiently robust to survive isolation to a useful degree of purity from a reaction mixture, and Formulation into an efficacious therapeutic agent.

The term "substituted", as used herein, means that any one or more hydrogen on the designated atom is replaced with a selection from the indicated group, provided that the designated atom's normal valency is not exceeded, and that the substitution results in a stable compound. When a substitent is keto (i.e., =O), then 2 hydrogens on the atom are replaced.

As used herein, "alkyl" is intended to include both branched and straight-chain saturated aliphatic hydrocarbon groups having the specified number of carbon atoms (for example, "$C_1-C_{10}$" denotes alkyl having 1 to 10 carbon atoms); "haloalkyl" is intended to include both branched and straight-chain saturated aliphatic hydrocarbon groups having the specified number of carbon atoms, substituted with 1 or more halogen (for example $-C_vF_w$ where v=1 to 3 and w=1 to (2v+1)); "alkoxy" represents an alkyl group of indicated number of carbon atoms attached through an oxygen bridge; "alkylthio" represents an alkyl group of indicated number of carbon atoms attached through a sulfur bridge; "dialkylamino" represents a N atom substituted with 2 alkyl groups of the indicated number of carbon atoms; "cycloalkyl" is intended to include saturated ring groups, including mono—,bi- or poly-cyclic ring systems, such as cyclopropyl, cyclobutyl, cyclopentyl, cyclohexyl, cycloheptyl, cyclooctyl, and adamantyl; and "bicycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl and the like; and "alkynyl" is intended to include hydrocarbon chains of either a straight or branched configuration and one or more triple carbon-carbon bonds which may occur in any stable point along the chain, such as ethynyl, propynyl and the like.

The terms "alkylene", "alkenylene", "phenylene", and the like, refer to alkyl, alkenyl, and phenyl groups, respectively, which are connected by two bonds to the rest of the structure of Formula I. Such "alkylene", "alkenylene", "phenylene", and the like, may alternatively and equivalently be denoted herein as "-(alkyl)-", "-(alkenyl)-" and "-(phenyl)-", and the like.

"Halo" or "halogen" as used herein refers to fluoro, chloro, bromo and iodo; and "counterion" is used to represent a small, negatively charged species such as chloride, bromide, hydroxide, acetate, sulfate and the like.

As used herein, "aryl" or "aromatic residue" is intended to mean phenyl or naphthyl; the term "arylalkyll" represents an aryl group attached through an alkyl bridge.

As used herein, "carbocycle" or "carbocyclic residue" is intended to mean any stable 3- to 7-membered monocyclic or bicyclic or 7- to 14-membered bicyclic or tricyclic or an up to 26-membered polycyclic carbon ring, any of which may be saturated, partially unsaturated, or aromatic. Examples of such carbocyles include, but are not limited to, cyclopropyl, cyclopentyl, cyclohexyl, phenyl, biphenyl, naphthyl, indanyl, adamantyl, or tetrahydronaphthyl (tetralin).

As used herein, the term "heterocycle" or "heteroaryl" or "heterocyclic" is intended to mean a stable 5- to 7- membered monocyclic or bicyclic or 7- to 10-membered bicyclic heterocyclic ring which may be saturated, partially unsaturated, or aromatic, and which consists of carbon atoms and from 1 to 4 heteroatoms independently selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl (pyridinyl), pyrimidinyl, furanyl (furyl), thiazolyl, thienyl, pyrrolyl, pyrazolyl, imidazolyl, tetrazolyl, benzofuranyl, benzothiophenyl, indolyl, quinolinyl, isoquinolinyl, benzimidazolyl, piperidinyl, pyrrolidinyl, 2-pyrrolinyl, tetrahydrofuranyl, tetrahydroquinolinyl, tetrahydroisoquinolinyl, decahydroquinolinyl, octahydroisoquinolinyl, pyranyl, isobenzofuranyl, 2H-pyrrolyl$_1$ isothiazolyl, isoxazolyl, oxazolyl, pyrazinyl, pyridazinyl, indolizinyl, isoindolyl, 3H-indolyl, 1H-indazolyl, pyrrolidinyl, pyrrolinyl, imidazolidinyl, imidazolinyl, pyrazolidinyl, pyrazolinyl, piperidinyl, piperazinyl, indolinyl, isoindoliflyl, morpholinyl or oxazolidinyl. Also included are fused ring and spiro compounds containing, for example, the above heterocycles.

As used herein, "pharmaceutically acceptable salts" refer to derivatives of the disclosed compounds wherein the parent compound of Formula I is modified by making acid or base salts of the compound of Formula I. Examples of pharmaceutically acceptable salts include, but are not limited to, mineral or organic acid salts of basic residues such as amines; alkali or organic salts of acidic residues such as carboxylic acids; and the like.

"Prodrugs" are considered to be any covalently bonded carriers which release the active parent drug according to Formula I in vivo when such prodrug is administered to a mammalian subject. Prodrugs of the compounds of Formula I are prepared by modifying functional groups present in the compounds in such a way that the modifications are cleaved, either in routine manipulation or in vivo, to the parent compounds. Prodrugs include compounds of Formula I wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds of Formula I, and the like.

The pharmaceutically acceptable salts of the compounds of Formula I include the conventional non-toxic salts or the quaternary ammonium salts of the compounds of Formula I formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the compounds of Formula I which contain a basic or acidic moiety by conventional chemical methods. Generally, the salts are prepared by reacting the free base or acid with stoichiometric amounts or with an excess of the desired salt-forming inorganic or organic acid or base in a suitable solvent or various combinations of solvents.

The pharmaceutically acceptable salts of the acids of Formula I with an appropriate amount of a base, such as an alkali or alkaline earth metal hydroxide e.g. sodium, potassium, lithium, calcium, or magnesium, or an organic base such as an amine, e.g., dibenzylethylenediamine, trimethylamine, piperidine, pyrrolidine, benzylamine and the like, or a quaternary ammonium hydroxide such as tetramethylammoinum hydroxide and the like.

As discussed above, pharmaceutically acceptable salts of the compounds of the invention can be prepared by reacting the free acid or base forms of these compounds with a stoichiometric amount of the appropriate base or acid, respectively, in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the educt molecule must be compatible with the reagents and reactions proposed. Not all compounds of Formula I falling into a given class may be compatible with some of the reaction conditions required in some of the methods described. Such restrictions to the substituents which are compatible with the reaction conditions will be readily apparent to one skilled in the art and alternate methods must then be used.

Compounds of Formula I wherein $R^1$ is a substituted aryl, X is a single bond (i.e. X is absent), $R^2$ is a 4-methylsulfonylphenyl and $R^3$, $R^4$, $R^7$ and $R^8$ are defined as above, can be prepared following the general method illustrated in Scheme 1.

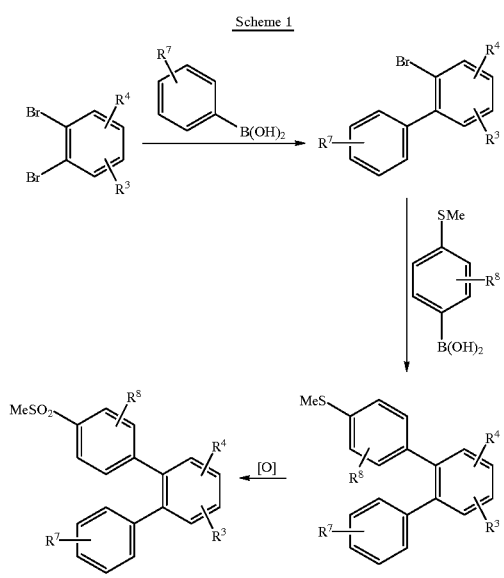

Coupling of a suitably substituted phenylboronic acid with an ortho-dibromobenzene using methodology introduced by Suzuki (A. Suzuki et al., J. Am. Chem. Soc., 1989, 11, 513 and V. N. Kalinin, Russ. Chem. Rev., 1991, 60, 173) affords a mixture of 2-bromobiphenyl A and 1,2-diarylbenzene. Suitable solvents for this coupling include but are not limited to toluene, dimethylformamide, dioxane and ethanol. The reaction is carried out in the presence of a palladium catalyst, for example, tetrakis triphenylphosphine palladium or bis(triphenyl-phosphine) palladium dichloride. Removal of the biscoupling product can be achieved using standard chromatographic techniques known to those skilled in the art of organic synthesis to give the desired biphenyl intermediate. A second Suzuki coupling of this 2-bromobiphenyl with a 4-methylthio-phenylboronic acid using the conditions described above provides 2-(4'-methylthio)phenyl-1-biphenyl. Oxidation of the methylthio group to the corresponding methylsulfonyl group gives a compound of Formula I. This oxidation can be accomplished using any of the reagents known in the art for the oxidation of mercaptans to sulfones. Examples of such reagents include, but are not limited to, oxone in methanol-water (Trost et. al. Tet. Lett. 22 (14), 1287, 1981), hydrogen peroxide, m-chloroperbenzoic acid, or monoperoxyphthalic acid, magnesium salt.

Alternatively, compounds of Formula I, wherein $R^1$ is a substituted aryl, X is a single bond, and $R^2$ is a 4-methylsulfonylphenyl can also be prepared from commercially available 2-bromophenols as depicted in Scheme 2.

Suzuki coupling of a 2-bromophenol with a phenylboronic acid can be carried out under the conditions described above using either the free or suitably protected phenol, or the corresponding triflate. A second Suzuki coupling between the intermediate triflate and a 4-methylthiophenylboronic acid followed by oxidation as previously described gives compounds of Formula I.

Scheme 2

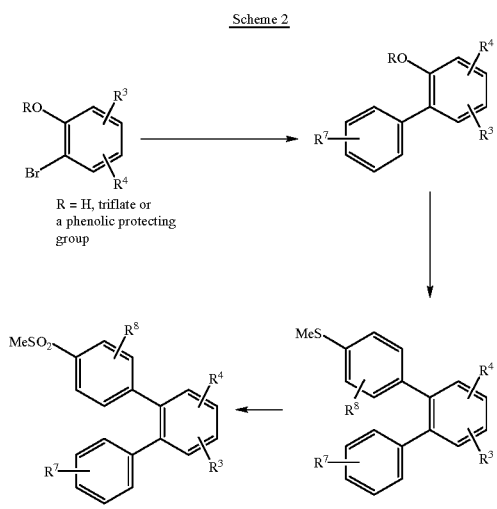

Compounds of Formula I wherein $R^2$ is a 4-methylsulfonylphenyl, X is a single bond and $R^1$ is a cycloalkenyl or cycloalkyl moiety, are prepared from 2-bromo-(4'-methylthio)biphenyls by the series of steps outlined in Scheme 3. The required biphenyl starting materials are obtained by Suzuki coupling of 1,2-dibromobenzene with 4-methylthiophenylboronic acid using conditions described above.

Treatment of 2-bromo-(4'-methylthio)biphenyl with a strong base at low temperature followed by the addition of a suitable cycloalkanone provides a (1-hydroxycycloalkyl)biphenyl intermediate. Suitable strong bases that can be used in this reaction include n-butyllithium, t-butyllithium, or methyllithium. The reaction is run in an aprotic solvent such as tetrahydrofuran, ether, hexane or 1,4-dioxane. Dehydration of the resulting tertiary alcohol can be readily accomplished by treatment with a catalytic amount of a strong acid, e.g. p-toluenesulfonic acid, in a suitable solvent, e.g. toluene. Oxidation of the methylthio group to the methyl sulfonyl as described above gives compounds of Formula I wherein $R^1$ is cycloalkenyl. Catalytic hydrogenation of these cycloalkenyl compounds over a suitable catalyst, for example, platinum oxide, in a suitable polar solvent, for example, methanol, provides compounds of Formula I wherein $R^1$ is cycloalkyl. Alternatively the cycloalkyl compounds may be obtained from the alcohol intermediate by first oxidizing the methylthio group to the methylsulfone followed by direct hydrogenation of the tertiary alcohols using the same hydrogenation conditions described above for the reduction of the olefin.

Scheme 3

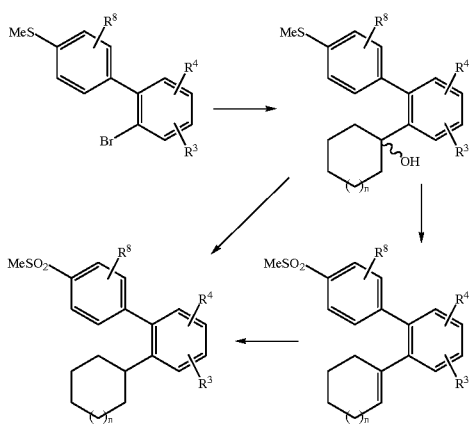

Compounds of Formula I wherein X is oxygen, $R^1$ is substituted or unsubstituted phenyl and $R^2$ is 4-methylsulfonylphenyl can be prepared from 2-hydroxy-(4'-methylthio)biphenyl as outlined in Scheme 4.

Scheme 4

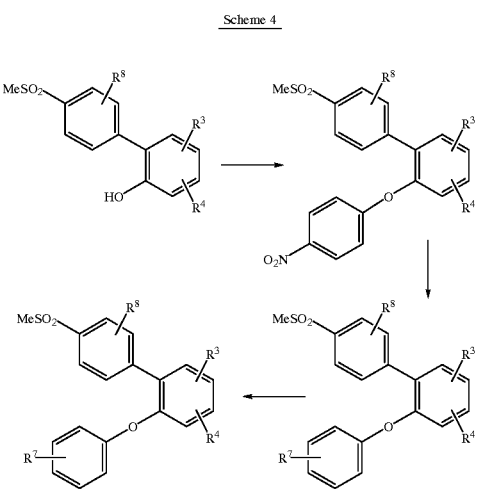

Treatment of 2-hydroxy-1-(4'-methylsulfonyl)-biphenyl (prepared via synthetic Scheme 2) with a suitable base, for example, sodium hydride, followed by the addition of 4-fluoro-1-nitrobenzene provides a 2-(4-nitrophenoxy)biphenyl intermediate. Reduction of the nitro group (see "Compendium of Organic Synthetic Methods" vol. 1 p. 266, 1971) gives a compound of Formula I where $R^7=NH_2$. Deamination can be achieved using the method of Cadogan, J. I. G. et. al. (J. Chem. Soc. Perkin. Trans. I 541, 1973). Alternately, the amine can be transformed into other functionalities via an intermediate diazonium salt using methods well known to one skilled in the art of organic synthesis. By employing this methodology other appropriately substituted aryl ethers of Formula I can easily be prepared.

Compounds of Formula 2 wherein $R^2$ is 4-methylsulfonylheteroaryl may be prepared by palladium-catalyzed Suzuki coupling of 2-biphenylboronic acid with an appropriately substituted 4-methylthioheteroaryl bromide or triflate (see Scheme 5). Oxone oxidation selectively provides the desired methylsulfonyl compounds.

Scheme 5

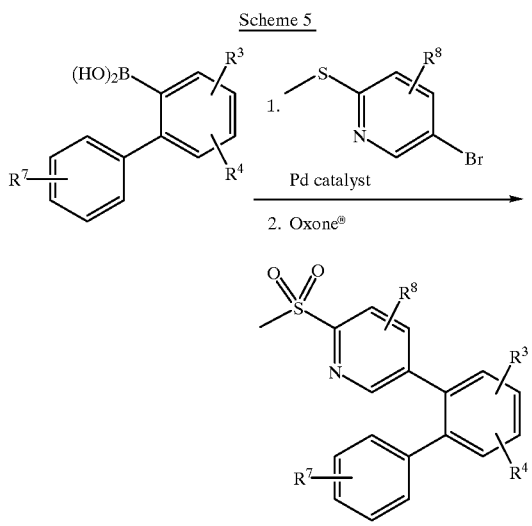

The 2-methylthio-5-bromo-pyridine reagents in Scheme 5 may be prepared in one step from commercially available 2,5-dibromopyridines as illustrated in Scheme 6 by treatment with an alkaline salt of methyl mercaptan, for example sodium methylthiolate, in a polar, aprotic solvent such as anydrous dimethylformamide.

Scheme 6

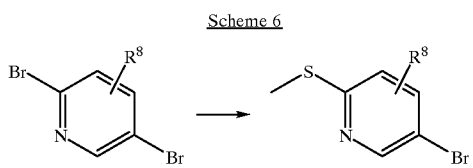

Other bromo or hydroxy methylthio heteroaryl starting materials that may be used in the Suzuki coupling to the 2-biphenylboronic acid may be easily prepared in a similar manner from commercially available starting materials.

For example, 2-bromo-5-methylthiopyridine may be prepared by the treatment of 2-methoxy-5-bromopyridine (Shiao. M. J. et. al. Syn. Comm. 20(19), 2971, 1990) with n-butyllithium in anhydrous tetrahydrofuran at −78° C., followed by quenching the reaction with dimethyldisulfide to afford 2-methoxy-5-methylthiopyridine. Demethylation provides 2-hydroxy-5-methylthiopyridine which upon reaction with phosphorousoxybromide yields the desired 2-bromo-5-methylthiopyridine starting material. (Scheme 7)

Scheme 7

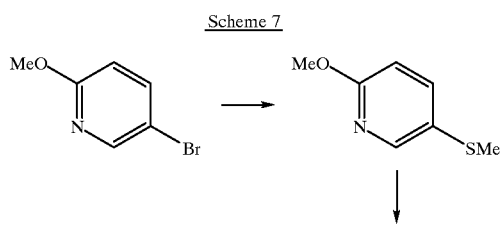

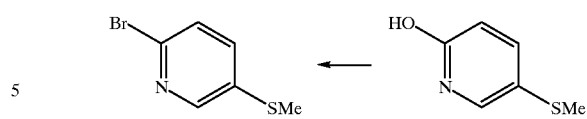

Compounds of Formula I wherein X is a single bond and $R^1$ is an aromatic heterocycle can be prepared by substitution of the appropriate bromoheteroaryl in place of the bromobenzene used for the Suzuki couplings described in the above Schemes. Suitable bromo-heteroaryls include, but are not limited to, 2- or 3-bromofuran, 2- or 3-bromothiophene, 3-bromopyridine, 2-bromobenzofuran (Baciocchi, E. et. al. J. Perk. Trans. II, 1976, 266) and 5-bromobenzothiophene (Worden et. al. J, Het. Chem. 25, 1271, 1988).

Compounds of Formula I wherein $R^8$ is other than H can be prepared using appropriately substituted 4-methylthiophenols as starting materials. These phenols may be prepared from commercially available starting materials by methods known in the art of organic synthesis. One such preparation is illustrated in Scheme 8, wherein 3-methyl-4-methylthioanisole is selectively demethylated to afford the corresponding phenol, which upon treatment with triflic anhydride in the presence of 2,6-lutidine in methylene chloride (Gerlach, U. et. al. Tet. Lett. 33(38), 5499, 1992), gives a triflate suitable for use in the above described palladium coupling procedures. The resulting methylthio intermediate can be converted into a compound of Formula I by oxidation to the corresponding sulfone as previously described.

Scheme 8

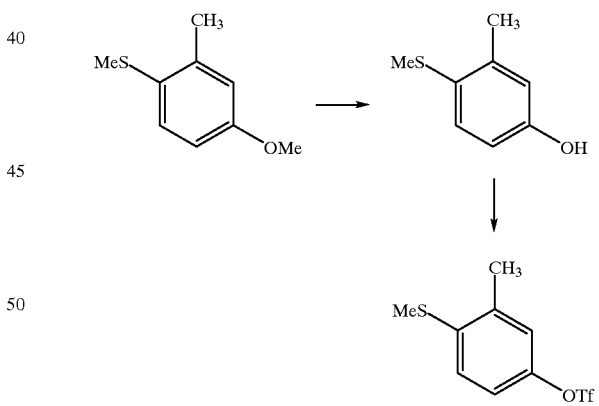

Compounds of Formula 1 wherein $R^3$ is other than hydrogen may be prepared through the use of appropriately substituted, commercially available bromobenzenes as starting materials for the Suzuki couplings described above. Standard functional group manipulations of the resulting compounds using methods well known to one skilled in the art of organic synthesis will provide additional $R^3$ substituents for which commercial starting materials are not available. The following Schemes serve to illustrate methods for the preparation of compounds of Formula I with a wide variety of $R^3$ substituents.

Scheme 9

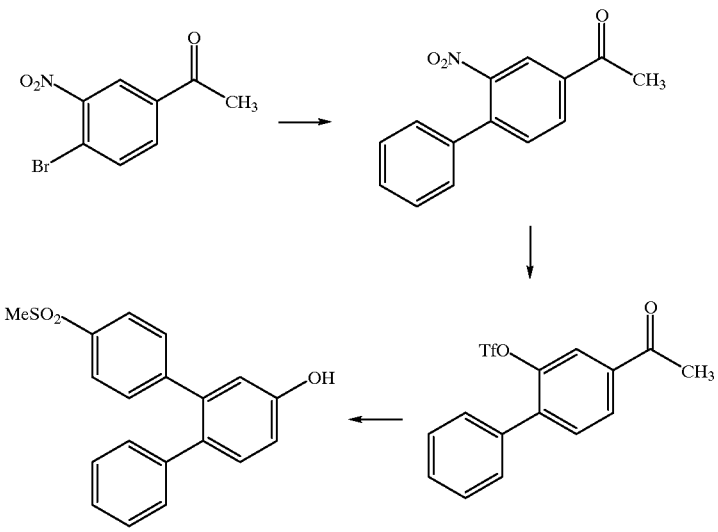

Palladium catalysed Suzuki coupling of 3-nitro-4-bromoacetophenone with phenylboronic acid affords 3-nitro-1-acetobiphenyl. Reduction of the nitro group with tin chloride in hydrochloric acid gives an amine which may be converted to the diazoniumfluoroborate by treatment with iso-amylnitrite and boron trifluoride etherate in methylene chloride (Doyle, M. P. et. al., J. Org. Chem. 44, 1572, 1979). The diazonium salt can then be converted directly to the triflate by treatment with trifluoroacetic acid (Yoneda, N. et. al. Chem. Lett. 1991, 459). Coupling of the triflate with 4-methylthiophenyl boronic acid as described above followed by oxidation with excess MCPBA (m-chloroperbenzoic acid) provides a compound of Formula I wherein $R^3$ is OH. (Scheme 9)

This compound can serve as the starting material for further compounds of Formula I as illustrated in Scheme 11. Conversion of the hydroxyl group to an ether may be achieved by alkylation with sodium hydride and an appropriate alkyl halide in anhydrous tetrahydrofuran. The hydroxyl group may also be converted to a triflate by treatment with triflic anhydride in the presence of 2,6-lutidine using methylene chloride as solvent. The resulting triflate can undergo a palladium catalysed Suzuki coupling (Cacchi et. al. Tet. Lett. 27(33), 3931, 1986; Kalinin, V. Synthesis 413, 1992) or Stille coupling (Stille, J. K. J. Am. Chem. Soc. 1988, 110, 1557) to afford substituted alkenyl, keto and carboxylic acid derivatives.

In addition to the transformations shown in Scheme 11, by employing techniques known in the art of organic synthesis, the esters may be saponified to the carboxylic acids which in turn may be converted to substituted amides, ketones, or hydroxamates. The alkene esters may also be reduced by catalytic hydrogenation to give the saturated esters using palladium on charcoal as catalyst.

Scheme 11

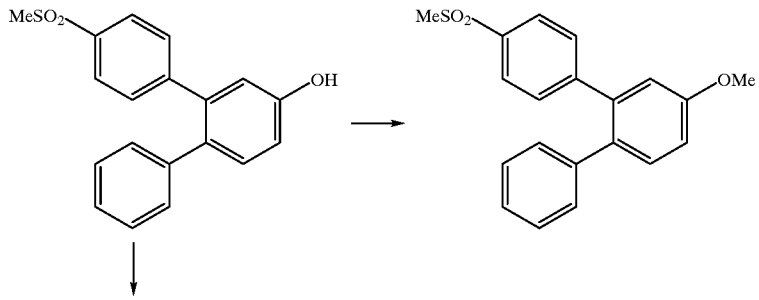

-continued

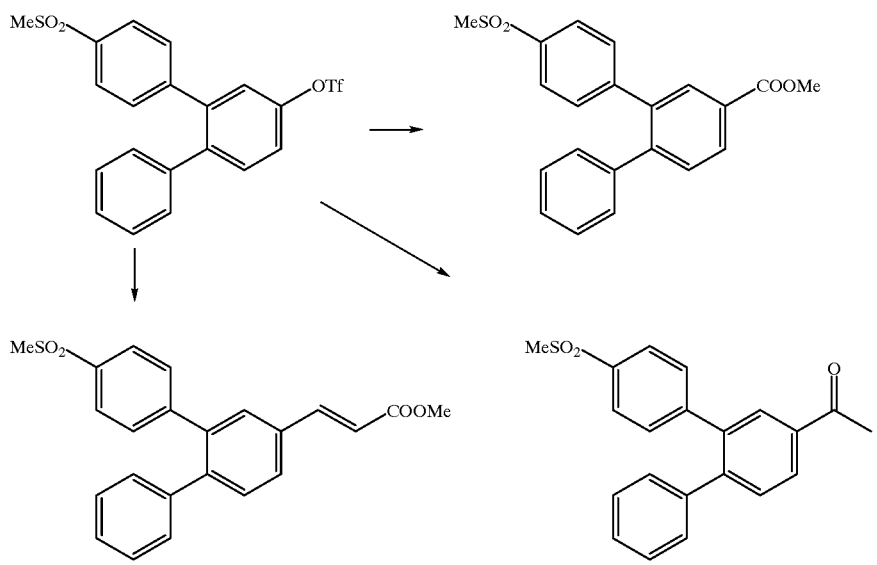

Compounds of Formula I wherein $R^3$ is an amine function, may be prepared from the intermediate 2-[4-methylthiophenyl]-4-aceto-1-biphenyl intermediates prepared in Scheme 9 as shown in Scheme 11a. Beckmann rearrangement (Donaruma, L. G. et al., Organic Reactions, Vol 11, 1–156, 1960) of the ketone followed by hydrolysis of the resulting amide provides an amine which may then be converted to amides, disubstituted amines or substituted amides by procedures known in the art of organic synthesis. Oxidation of the methylthio group as previously described gives compounds of Formula I. Alternatively compounds wherein $R^3$ is an amino function may also be obtained from carboxylic acids via the "Curtius rearrangement" (Banthorpe, D. V. in "The Chemistry of the Azido Group," Palai, S. Ed., Interscience, New York, 1971, pp 397–405) as shown in Scheme 12b.

Scheme 12a

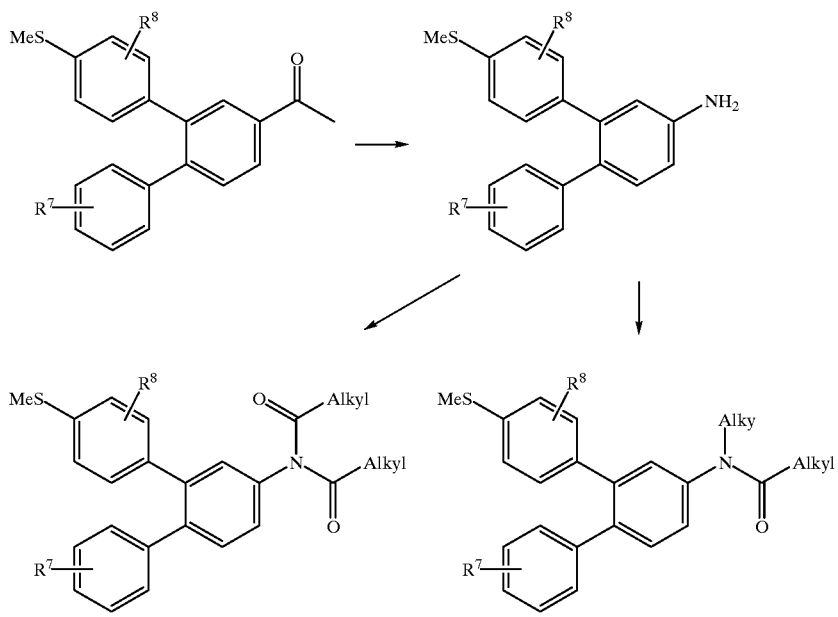

Scheme 12b

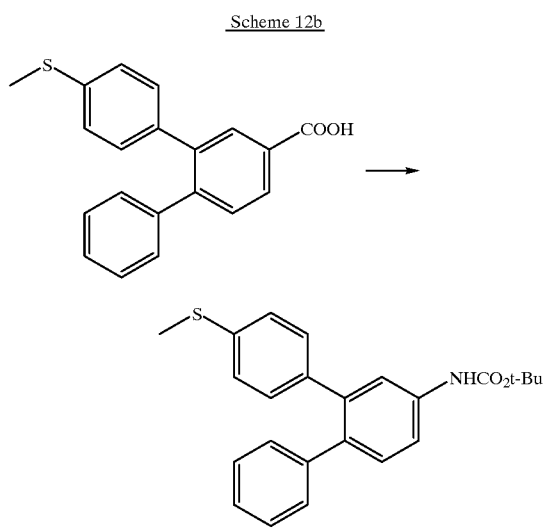

Compounds of Formula I wherein $R^3$ and $R^4$ are both other than hydrogen may be obtained via various methods known in the art. One such route is depicted in Scheme 13.

Scheme 13

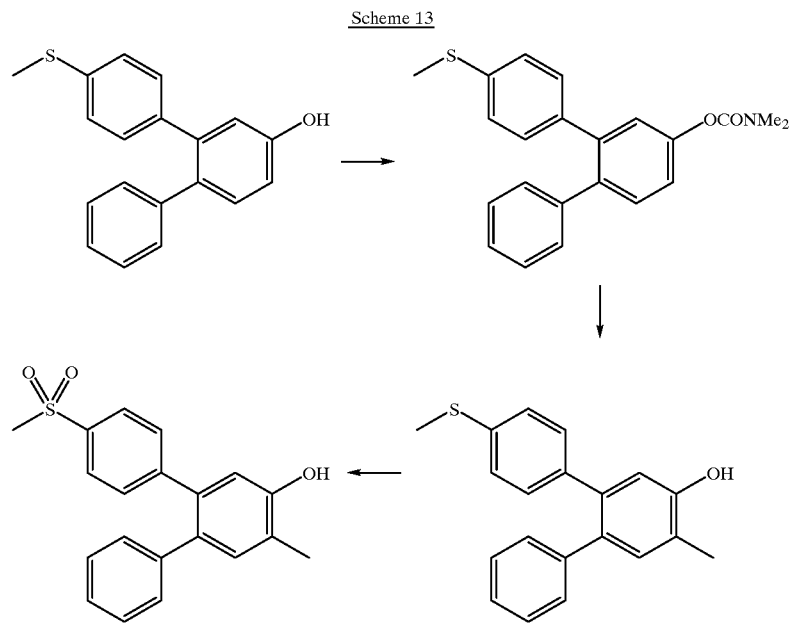

Conversion of 3-(4'-methylthio)phenyl-1-hydroxy-4-biphenyl (prepared as described for Scheme 12) to a N,N-dimethylcarbamate can be achieved by reaction with sodium hydride and N,N-dimethylcarbamoyl chloride in anydrous tetrahydrofuran. Directed orthometallation (Snieckus, V. Chemical Reviews, 1990, 879) using sec-butyl lithium in anydrous tetrahydrofuran followed by quenching the resulting anion with an appropriate electrophile (e.g. methyl iodide) affords an intermediate which can be converted to various compounds of Formula I using methods described above or known to one skilled in the art of organic synthesis.

Compounds of Formula I wherein one or more of J, K, or L is nitrogen can be prepared by substitution of an appropriately functionalized heterocycle for the bromo or dibromobenzenes in the above Schemes. For example for the case where J is nitrogen, the synthesis of a compound of Formula I is illustrated in Scheme 14.

Scheme 14

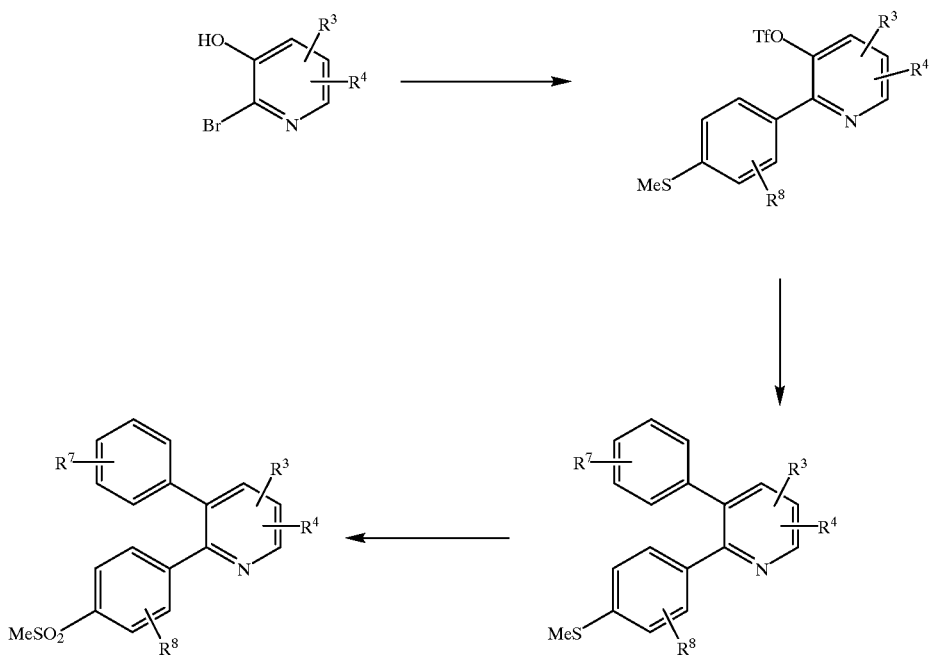

Palladium catalysed Suzuki coupling of 2-bromo-3-hydroxypyridine with an appropriately substituted phenylboronic acid provides a 2-phenyl-3-hydroxypyridine. Conversion of the hydroxy group to the triflate under conditions previously described followed by an anydrous palladium catalysed Suzuki coupling with 4-methylthiophenylboronic acid affords a 2,3-diarylpyridine. A suitable solvent for this coupling is anhydrous 1,4-dioxane. Selective oxidation of the methylthio group can be accomplished by treatment with oxone to give compounds of Formula I wherein J is N.

Compounds of Formula I wherein X is a single bond and $R^1$ is 1-piperidinyl or I-pyrrolyl can be prepared from 2-bromoaniline as shown in Scheme 15. Suzuki coupling of 2-bromoaniline with 4-thiomethylphenylboronic acid using the method described above followed by condensation of the resulting 2-(4-methylthiophenyl)aniline with dibromopentane in the presence of an amine base, such as triethylamine, affords the corresponding 1-[2-(4-methylthiophenyl)phenyl] piperidine. Oxidation if the methylthio to the methylsulfonyl using methods described above provides compounds of Formula I wherein $R^1$ is 1-piperidinyl. Alternately the starting 2-bromoaniline can be converted to the 1-[(2-bromophenyl)phenyl]pyrrole by treatment with 2,5-dimethoxytetrahydrofuran in glacial acetic acid. Suzuki coupling of the resulting intermediate with 4-methylthiophenylboronic acid followed by oxidation, as described above, gives the 1-[2-(4-methylsulfonylphenyl) phenyl]pyrrole.

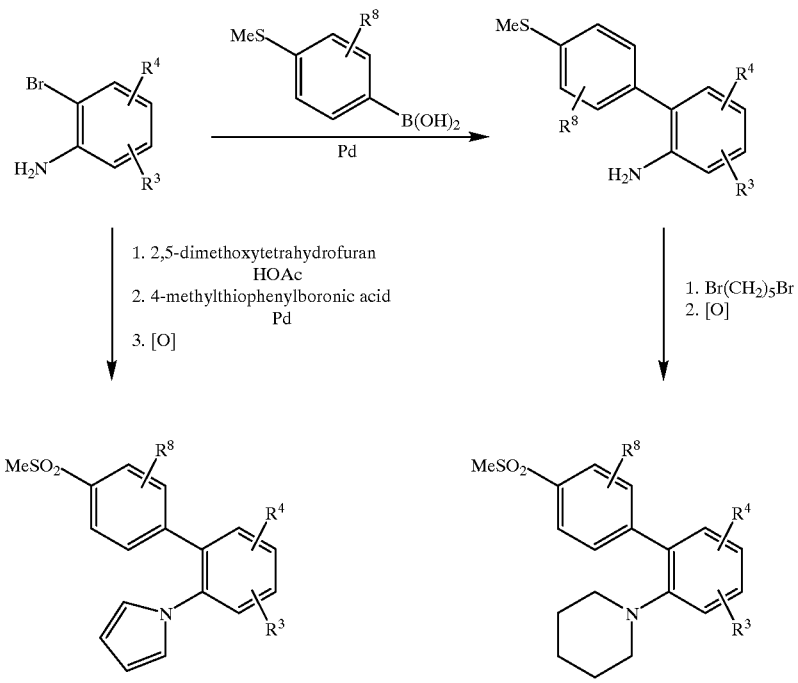

The compounds of this invention and their preparation can be further understood by the following procedures and examples, which exemplify but do not constitute a limit of their invention.

EXAMPLES

All melting points are uncorrected. All reactions were conducted under a nitrogen atmosphere except where otherwise noted. All commercial chemicals were used as received. Chromatography was performed with Merck silica gel 60 (230–400 mesh). The chromatography eluents are given as ratios by volume. Organic phases from solvent-solvent extractions were generally dried over magnesium sulfate, unless otherwise noted. Solvents were generally removed by evaporation under reduced pressure on a rotary evaporator unless otherwise noted. Peak positions for $^1$H NMR spectra are reported as parts per million (d) downfield from the internal standard tetramethylsilane. Abbreviations for $^1$H NMR spectra are as follows: s=singlet, d=doublet, m=multiplet, dd=doublet of doublets. Mass spectra were obtained using chemical ionization with ammonia as the reagent gas. Microanalyses were performed by Quantitative Technologies Inc., Bound Brook, N.J.

Example 1

2-[(4-methylthio)-phenyl]-1-biphenyl (method 1)

A. 4-Methylthiophenyl boronic acid: To magnesium filings (4.3 g, 180 mmol) cooled to 0° C. was slowly added a 1M solution of borane-tetrahydrofuran complex (600 ml, 600 mmol). To the resulting mixture was added dropwise a suspension of 4-bromothioanisole (30 g, 148 mmol) in tetrahydrofuran ( 75 ml). A few crystals of iodine were added, and the reaction was allowed to warm to room temperature and was stirred for 72 h. The reaction was carefully poured onto 500 g of crushed ice. The solution was made acidic (pH 3) with 1N hydrochloric acid and allowed to sit overnight. The acidic solution was extracted with diethyl ether. The diethyl ether was extracted with 1N sodium hydroxide. The sodium hydroxide layer was acidified and then extracted with diethyl ether. Evaporation of solvent gave colorless crystals which were recrystallized from ethyl acetate and a small amount of water to provide 12.5 g of 4-methylthiophenyl boronic acid; $^1$H NMR (DMSO) d 7.73 (d, J=8.42 Hz, 2H), 7.21 (d, J=8.42 Hz, 2H), 2.47 (s, 3H); Mass spectrum (CI, CH$_4$) m/z 195 (M+H$^+$) ethylene glycol ester).

B. 2-bromo-1-(4'-methylthiophenyl) benzene: A mixture of 4-methylthiophenyl boronic acid (31.1 g, 185 mmol), 1,2-dibromobenzene (35 g, 148 mmol), and tetrabutylammonium bromide (1 g, 3.10 mmol) in ethanol (125 ml) and toluene (250 ml) was degassed by bubbling nitrogen through the mixture for 15 minutes. 2M Sodium carbonate (148 ml, 296 mmol) was degassed and added to the mixture. Tetrakis (triphenylphosphine)palladium (0.35 g, 0.303 mmol) was added and the mixture heated to reflux for 24 h. The reaction was cooled to room temperature and filtered to remove solids. The filtrate was concentrated and then diluted with water and ethyl acetate. The aqueous layer was extracted with ethyl acetate. The organic layers were combined and washed with brine and dried over sodium sulfate. The ethyl acetate was concentrated and a precipitate formed. The additional precipitate formed when diethyl ether (200 ml) was added. The precipitate was removed via filtration and the filtrate concentrated to give a crude oil. Purification by column chromatography on silica gel using hexane as eluant provided the desired product (25.75 g., 62%) which solidified on standing, mp 33–35 ° C.; $^1$H NMR (CDCl$_3$) d 7.66 (d, J=8.05 Hz, 1H), 7.36–7.28 (m, 6H), 7.21 (m, 1H), 2.52 (s, 3H); Mass spectrum m/z 279.1, 281.1 (M+H); Analysis for C$_{13}$H$_{11}$BrS: Calc'd C: 55.92%, H: 3.97%, Br: 28.62%; found C: 56.24%, H: 4.04%, Br: 28.96%.

C. 2-Bromo-1-(4'-methylsulfonylphenyl)benzene: The compound of Ex. 1, part B (5.2 g, 18.7 mmol) was dissolved in dichloromethane (100 ml) and cooled to 0° C. 3-Chloroperbenzoic acid (8.9 g, 41.2 mmol) was added and the mixture was stirred at room temperature for 18 h. The reaction was diluted with dichloromethane and washed successively with sodium bicarbonate, dilute sodium bisulfite, dried over sodium sulfate, filtered and concentrated. Purification by chromatography on silica gel using 7:1 hexane/ethyl acetate as eluant provided a colorless crystals which were recrystallized (dichloromethane/hexane) to give the pure product (4.02 g, 69%), mp 155–157° C.; $^1$H NMR (CDCl$_3$) d 8.02 (d, J=8.42 Hz, 2H), 7.71 (d, J=6.96 Hz, 1H), 7.63 (d, J=8.42 Hz, 2H), 7.43 (m, 1H), 7.32 (m, 2H), 3.13 (s, 3H); IR (KBr) 1306, 1142 cm$^{-1}$; Analysis for C$_{13}$H$_{11}$BrO$_2$S:calc'd C: 50.17%, H: 3.56%, S: 10.30%; found C: 50.09%, H: 3.41%, S: 10.52%.

D. 2-[(4-methylthio)phenyl]-1-biphenyl: 2-Bromo-1-(4'-methylsulfonylphenyl)benzene (4 g, 12.8 mmol), phenyl boronic acid (1.72 g, 14 mmol), and tetrabutylammonium bromide (0.21 g, 0.65 mmol) were dissolved in toluene (70 ml) and ethanol (35 ml) and degassed by bubbling nitrogen through for 15 minutes. Degassed 2M sodium carbonate (14 ml, 28 mmol) and tetrakis(triphenylphosphine)palladium (0.074 g, 0.064 mmol) were added and the mixture was heated to reflux for 4 h. The reaction was concentrated and diluted with water and ethyl acetate. The layers were separated and the aqueous layer extracted with ethyl acetate. The combined organic layers were washed with brine, dried, filtered and concentrated. Purification by column chromatography on silica gel using 3:1 hexane/ethyl acetate as eluant and recrystallization (dichloromethane/hexane) afforded 2.55 g (65%) of the title compound as colorless crystals, mp 136–138° C.; $^1$H NMR (CDCl$_3$) d 7.79 (d, J=8.42 Hz, 2H), 7.47 (m, 3H), 7.42 (m, 1H), 7.34 (d, J=8.7 Hz, 2H), 7.23 (m, 3H), 7.11 (m, 2H) 3.04 (s, 3H); Mass spectrum (CI, CH$_4$) m/z 309 (M+H), 337 (M+C2H5); Analysis for C$_{19}$H$_{16}$O$_2$S: calc'd C: 74.00%, H: 5.23%, S: 10.40%; found C: 74.01%, H: 5.13%, S: 10.63%.

Example 1a

2-[(4'-methylthio)phenyl]-1-biphenyl (Method 2)

A. 2-Phenyl-1-phenoxytrifluoromethane sulfonate: A mixture of 2-Phenylphenol (5 g, 29.4 mmol), N,N-dimethylaminopyridine (0.61 g, 4.99 mmol), and 2,6-lutidine (4.1 ml, 35.0 mmol) in dichloromethane (180 ml) was cooled to −30° C. Trifluoromethanesulfonic anhydride (5.90 ml, 35.0 mmol) was added and the cooling bath was removed. After 1 h at room temperature the mixture was washed with 0.5N HCl, water, saturated sodium bicarbonate, brine. The mixture was dried, filtered and concentrated to afford the desired triflate (8.80 g., 99%) as a yellow oil; $^1$HNMR (CDCl$_3$) d 7.35–7.50 (m, 9H); Mass spectrum (CI, CH$_4$) m/z 303 (M+H), 331 (M+C$_2$H$_4$).

B. 2-[(4'-methylthio)phenyl]-1-biphenyl: 2-Phenyl-1-phenoxytrifluoromethane sulfonate (13.75 g, 45.5 mmol), 4-methylthio benzene boronic acid (8.4 g, 50.0 mmol), and potassium phosphate tribasic (12.6 g, 59.0 mmol) were suspended in 1,4-dioxane and degassed by bubbling nitrogen through for 30 minutes. Tetrakis(tri-phenylphosphine) palladium (1.30 g, 1.14 mmol) was added and the mixture was heated to reflux for 24 h. The mixture was cooled, filtered and concentrated. The residue was dissolved in ethyl acetate and washed with water and brine and dried. Purification by chromatography on silica gel using hexane as eluant and recrystallization (EtOH) afforded the desired product (4.27 g) as white crystals, mp 42–44° C. Concentration of the mother liquor afforded an additional 4.98 g of product; $^1$H NMR (CDCl$_3$) d 7.41 (s, 4H), 7.23 (m, 3H), 7.16 (m, 2H), 7.13–7.04 (m, 4H), 2.45 (s, 3H); Mass spectrum m/z 277.1 (M+H), 294.1 (M+NH$_4$); Analysis for C$_{19}$H$_{16}$S cal'd C: 82.56%, H: 5.84%, S: 11.60%; found C: 82.39%, H: 5.77%, S: 11.60%.

C. 2-[(4'-methylthio)phenyl]-1-biphenyl: 4'-Methylthiophenyl-2-phenylbenzene (2.0 g, 7.30 mmol) was dissolved in dichloromethane (60 ml) and cooled to 0° C. 3-Chloroperbenzoic acid (3.40 g, 15.9 mmol) was added and the mixture was stirred 3 h. The mixture was washed with sodium bicarbonate, sodium bisulfate, brine, and dried. Purification by chromatography on silica gel using 4:1 hexane/ethyl acetate as eluant and recrystallization (dichloromethane/hexane) afforded the title compound (0.64 g., 28.6%) as a crystalline solid, mp 135–137° C.; $^1$H NMR (CDCl$_3$) d 7.79 (d, J=8.42 Hz, 2H), 7.47 (m, 3H), 7.42 (m, 1H), 7.34 (d, J=8.7 Hz, 2H), 7.23 (m, 3H), 7.11 (m, 2H) 3.04 (s, 3H); Mass spectrum m/z 309 (M+H), 326 (M+NH$_4$); IR (KBr): 1312, 1154, 760 cm$^{-1}$; Analysis for C$_{19}$H$_{16}$O$_2$S: calc'd C: 74.00%, H: 5.23%, S: 10.40%; found C: 74.07%, H: 5.17%, S: 10.37%.

Example 109

1-Cyclohexene-2-(4'-methylsulfonylphenyl)benzene

A. 2-(4'-methylthiophenyl)-1-(1-hydroxy-1-cyclohexyl)-benzene: 2-Bromo-(4'-methylthiophenyl) benzene (3.02 g, 10.8 mmol) was dissolved in tetrahydrofuran (35 ml), cooled to −78° C. and n-butyllithium (4.5 ml, 11.3 mmol) was slowly added. The pale yellow mixture was stirred at −78° C. for 2 h followed by addition of cyclohexanone (1.3 ml, 12.9 mmol). The reaction was stirred for 18 h and allowed to warm to room temperature. The reaction was diluted with water and ethyl acetate. The aqueous layer was extacted with ethyl acetate and the combined organic layers were dried, filtered and concentrated. Purification by chromatography on silica gel using 6:1 hexane/ethyl acetate as eluant afforded the desired product (2.51 g., 77%) as a clear oil; $^1$H NMR (CDCl$_3$) d 7.58 (d, 1H), 7.36 (m, 2H), 7.27 (m, 4H), 7.04 (dd, 1H), 2.53 (s, 3H), 2.34 (t, 1H), 1.83–1.10 (m, 10H), Mass spectrum (high resolution, EI/DEP) calc'd M+ 298.139137; found M+ 298.138665.

B. 1-Cyclohexene-2-(4'-methylthiophenyl)benzene: the compound of Ex. 109, part A (2.17 g, 7.27 mmol) was dissolved in toluene (30 ml) and a catalytic amount of p-toluene sulfonic acid (0.05 g) was added. The mixture was heated to reflux. After 4 h the mixture was cooled and washed with sodium bicarbonate, dried, filtered and concentrated. Purification by chromatography on silica gel using 4:1 hexane/ethyl acetate as eluant and recrystallization (methanol) afforded the cycloalkene (1.29 g., 65%) as white crystals, mp 71–73° C. Concentration of the mother liquor afforded 0.15 g additional product; $^1$H NMR (CDCl$_3$) d 7.37 (d, J=8.42 Hz, 2H), 7.28 (m, 6H), 5.67 (m, 1H), 2.52 (s, 3H), 2.09 (m, 2H), 1.83 (m, 2H), 1.53 (m, 4H); Analysis for C$_{19}$H$_{20}$S: calc'd C: 81.38%, H: 7.19%, N: 11.43%; found C: 81.17%, H: 7.16%, S: 11.53%.

C. 1-Cyclohexene-2-(41-methylsulfonylphenyl) benzene: The compound of Ex. 109, part B (1.35 g, 4.80 mmol) was suspended in methanol (125 ml), cooled to 0° C., and Oxone (8.30 g, 13.0 mmol) in water (50 ml) was added. The thick suspension was allowed to warm to room temperature and was stirred 18 h. The mixture was diluted with water (200 ml) and a white crystalline solid was collected. The product was rinsed with water, dilute sodium bisulfite, and water. The product was dried in vacuo. Purification by chromatography on silica gel using 4:1 hexane/ethyl acetate as eluant and recrystallization (methanol) afforded the title compound (0.524 g.,35%) as colorless crystals, mp 126–128° C. Concentration of the mother liquor afforded an additional 0.278 g of product; $^1$H NMR (CDCl$_3$) d 7.95 (d, J=8.42 Hz, 2H), 7.63 (d, J=8.42 Hz, 2H), 7.36–7.25 (m, 4H), 5.63 (m, 1H), 3.10 (s, 3H), 2.06 (m, 2H), 1.84(m, 2H), 1.51–1.45 (m, 4H);

Analysis for $C_{19}H_2O_2S$: calc'd C: 73.04%, H: 6.45%, S: 10.26%; found C: 73.22%, H: 6.47%, S: 10.46%.

Example 130

3- (4'-methylsulfonylphenyl)-4-phenylphenol

A. 3-nitro-4-phenylacetophenone: A mixture of 4-bromo-3-nitroacetophenone (2.0 g, 8.19 mmol), phenyl boronic acid (1.2 g, 9.83 mmol), and tetrabutylammonium bromide (0.13 g, 0.41 mmol) in 2M sodium carbonate (35 ml), ethanol (20 ml), and toluene (65 ml) was degassed by bubbling nitrogen through for 30 minutes. The mixture was heated to reflux for 4 h. The reaction was cooled and the layers were separated. The aqueous layer was extracted with ethyl acetate and the combined organic layers were dried, filtered and concentrated. Purification by chromatography on silica gel using 4:1 Hexane/ethyl acetate as eluant afforded the desired product (1.98 g., 89%) as a yellow powder; $^1$H NMR (CDCl$_3$) d 8.39 (d, 1H), 8.16 (dd, 1H), 7.57 (d, 1H), 7.43 (m, 3H), 7.32 (dd, 2H), 2.69 (s, 3H); Mass spectrum 242.1 (M+H).

B. 3-amino-4-phenylacetophenone: A mixture of the product of Ex. 130, part A (2.0 g, 8.29 mmol), tin chloride (8.23 g, 36.48 mmol), ethanol (30 ml) and concentrated hydrochloric acid (7 ml) was heated at reflux for 2.5 h. The reaction was cooled to 0° C. and basified (pH 10) with 6M NaOH and extracted with ethyl acetate. The extract was dried and filtered through silica gel. The filtrate was concentrated and refiltered through silica gel using chloroform as eluant. The solvent was concentrated to give the amine (1.20 g., 69%) as a yellow powder; $^1$H NMR (CDCl$_3$) d 7.47 (d, 1H), 7.46 (s, 3H), 7.38 (dd, 2H), 7.36 (d, 1H), 7.20 (d, 1H), 3.90 (s, 2H), 2.60 (s, 3H); Mass spectrum m/z 212.1 (M+H).

C. 5-Aceto-2-phenylbenzene diazionium tetrafluoroborate: The compound of Ex. 130, part B (0.50 g, 2.36 mmol) was dissolved in dichloromethane (3 ml) and added slowly to boron trifluoride etherate in dichloromethane (10 ml) at −15° C. A solution of isoamylnitrite (0.35g, 2.60 mmol) in dichloromethane (3 ml) was added, the ice bath was removed and a brown precipitate formed. Pentane (20 ml) was added and the mixture was re-cooled to −15° C. for 20 minutes. Filtering afforded the diazonium salt (0.76 g) as a light brown powder; $^1$H NMR (CDCl3) d 9.55 (d, 1H), 8.71 (dd, 1H), 7.90 (d, 1H), 7.69 ( s, 5H), 2.79 ( s, 3H).

D. 5-Aceto-2-phenylbenzene trifluoromethanesulfonate: 5-Aceto-2-phenylbenzene diazonium tetrafluoroborate (1.46 g, 4.79 mmol) was slowly added to trifluoromethanesulfonic acid (10 ml) at −15° C. The mixture was heated to 50° C. for 20 minutes then poured onto ice (25 g). The aqueous layer was extracted with ethyl acetate, dried, filtered, and concentrated. Purification by chromatography on silica gel using 4:1 hexane/ethyl acetate as eluant afforded the triflate (0.428 mg., 77%) as a brown syrup; $^1$H NMR (CDCl$_3$) d 8.04 (dd, 1H), 7.96 (d, 1H), 7.62 (d,1H), 7.48 (s, 5H), 2.67 (s, 3H); Mass spectrum m/z 345 (M+H).

E. 3-(4'-Methylthiophenyl)-4-phenylacetophenone: A mixture of the compound of Ex. 130, part D (1.22 g, 3.54 mmol), 4-methylthiophenylboronic acid (0.71 g, 4.25 mmol), and tribasic potassium phosphate (1.13 g, 5.32 mmol) in 1,4-dioxane was degassed by bubbling nitrogen through for 15 minutes. Tetrakis(triphenylphosphine) palladium (0.10 g, 0.089 mmol) was added and the mixture was heated at reflux for 18 h. The mixture was cooled, filtered and concentrated. Purification by chromatography on silica gel using 4:1 hexane/ethyl acetate as eluant afforded the desired product (1.02 g., 90%) as a brown syrup; $^1$H NMR (CDCl3) d 7.99 (d, 2H), 7.53 (d, 1H), 7.48 (s, 2H), 7.27 (d,s, 2H), 7.17 (dd, 2H), 7.14 (q, 3H); Mass spectrum m/z 319 (M+H).

F. 3-(4'-Methylsulfonylphenyl)-4-phenylphenol: To the product of Ex. 130, part E (0.30 g, 0.942 mmol) was added peracetic acid (10 ml) and then concentrated sulfuric acid (0.25 ml). The mixture was stirred at room temperature for 48 h. The mixture was poured onto a mixture of ice and 20% sodium bisulfite (10 ml). The aqueous mixture was extracted with ethyl acetate, and the organic layers were dried, filtered and concentrated. Purification by repeated chromatography on silica gel using 2:1 hexane/ethyl acetate as eluant afforded the title compound (0.064 g., 21%) as a white powder; $^1$H NMR (CDCl$_3$) d 7.79 (d, 2H), 7.35 (d, 1H), 7.34 (d, 2H), 7.21 (d, 1H), 7.19 (d, 2H), 7.06 (m, 2H), 6.97 (dd, 1H), 6.90 (d, 1H), 4.96 (s, 1H), 3.05 (s, 3H); High resolution mass spectrum m/z calc'd: 342.1, found: 342.116391 (M+NH$_4$).

Example 151

1-[2-(4-methylsulfonylphenyl)phenyl]piperidine

A. 2-[(4-methylthio)phenyl]aniline: A mixture of 2-bromoaniline (2.0 g, 11.62 mmol), 4-methylthiophenyl boronic acid (2.3 g, 13.69 mmol), tetrabutylammonium bromide (0.19 g, 0.58 mmol), and 2M sodium carbonate (12 ml) in 85 ml of 2:1 toluene/ethanol were degassed by bubbling nitrogen through for 10 minutes. Tetrakis (triphenylphosphine) palladium (54 mg, 0.047 nmmol) was added and the mixture was heated to reflux for 5 h. The reaction mixture was cooled, concentrated, and diluted with ethyl acetate and water. The aqueous layer was extracted with ethyl acetate and the combined organic layers were dried (MgSO$_4$), filtered and concentrated. The crude product was chromatographed (hexane/ethyl acetate) to give a solid (1.4 g, 56%). mp 70–72° C.: NMR (CDCl$_3$) d 7.41–7.32 (m, 4H), 7.18–7.09 (m, 2H), 6.85–6.75 (m, 2H), 3.75 (brd. m, 2H), 2.53 (s, 3H) ppm; mass spec (NH$_3$-CI) m/z 215.9 (M+H$^+$, 100%).

Part B. 1-[2-(4-methylthiophenyl)phenyl]piperidine: To a mixture of the product from part A (0.3 g, 1.39 mmol), ethanol (10 ml), and triethylamine ( 0.39 ml, 2.77 mmol) was added 1,5 dibromopentane (0.29 ml, 2.08 mmol). The mixture was heated to reflux for 48h, then concentrated and chromatographed (hexanes) to give a pink oil (0.147 g, 37%). NMR (CDCl$_3$) d 7.73 (d, 2H), 7.39 (d, 2H) 7.36–7.30 (m, 2H), 7.15–7.10 ( m, 2H), 2.87–2.85 (m, 4H), 2.62 (s, 3H), 1.55 (s, 6H); mass spec (NH$_3$-CI) m/z 284.2 (M+H+, 100%).

Part C. 1-[2-(4-methylsulfonylphenyl)phenyl]piperidine: To a mixture of the compound of Ex. 195, part C (0.145 g, 0.512 mmol) in methanol (15 ml), cooled to 0° C., was added Oxone™(0.79 g, 1.28 mmol). The reaction was stirred at room temperature overnight. The reaction was diluted with methylene chloride and extracted. The combined organic layers were washed with sodium bicarbonate, sodium bisulfite, brine and dried (MgSO$_4$). The crude product was chromatographed (hexanes/ethyl acetate) and recrystallized (methylene chloride/hexanes) to give a solid (50 mg, 31%). mp 140–140.50° C. $^1$H NMR (CDCl$_3$) d 7.97–7.85 (dd, 4H), 7.36 (t, 1H), 7.23–7.20 (dd, 1H), 7.10–7.05 (m, 2H), 3.10 (s, 3H), 2.75 (m, 4H), 1.43 (m, 6H); High resolution mass spec calc'd for $C_{18}H_{21}NSO_2$: 316.137126; found: 316.136504.

Example 153

1-[2-(4'methylsulfonylphenyl)phenyl]pyrrole

A. 1-(2-bromophenyl)pyrrole: A mixture of 2-bromoaniline (1.72 g, 10 mmol), 2,5-dimethoxytetrahydrofuran (1.32 g, 10 mmol) and glacial acetic acid (4.5 ml) was stirred at reflux for 2 h under an atmosphere of nitrogen. The mixture was allowed to cool to room temperature. Solvent was removed under reduced pressure and the residue was purified by flash column chromatography (9:1 hexanesethyl acetate) to provide the desired pyrrole (1.85 g., 8.33 mmol, 83.3%) as a clear liquid. $^1$HNMR (CCDl$_3$) d 7.70–6.35 (m, 8H); IR(KBr) 3102, 1588 cm$^{-1}$; Mass Spec m/z 221.9 (M+H)$^+$.

B. 1-(2-(4-Methylthiophenyl)phenyl)pyrrole: A mixture of 1-(2-bromophenyl)pyrrole (0.666 g, 3.0 mmol), 4-methylthiophenylboronic acid (0.554 g., 1.1 eq.), 2M aqueous sodium carbonate solution (6 ml) and toluene (30 ml) was stirred at room temperature under an atmosphere of nitrogen. Nitrogen gas was bubbled through the solution for 20 min. To this mixture was added tetrakistriphenylphosphine palladium (100 mg, catalytic) and the mixture stirred at reflux for 4 h. The resulting mixture was allowed to cool to room temperature and was poured into 100 ml water. The mixture was extracted with three 100 ml portions of ethyl acetate. The combined organic layers were dried over anhydrous magnesium sulfate, filtered and solvent was removed under reduced pressure. The residue was purified by flash column chromatography (29:1 hexanes-ethyl acetate) to provide the coupling product as an oil (0.74 g., 2.79 mmol, 92.9%). $^1$HNMR (CDCl$_3$) d 7.44–6.16 (m, 12H) 2.46 (s, 3H); IR (neat): 2918, 1596 cm$^{-1}$; Mass Spec m/z 266.0 (M+H)$^+$.

C. 1-[2-(4-methylsulfonylphenyl)phenyl]pyrrole: A mixture of 1-(2-(4-methylthiophenyl)phenyl)pyrrole (0.74 g., 2.788 mmol), and methylene chloride (35 ml) was stirred and cooled in a salt/ice water bath under an atmosphere of nitrogen. To this was added in one portion, 3-chloroperoxybenzoic acid (50–60%, 1.924 g., >2 eq.). The solution was allowed to warm to room temperature and stirred overnight. The mixture was poured into saturated sodium bisulfite solution and extracted with three 50 ml portions of methylene chloride. The combined organic layers were washed with saturated sodium bicarbonate, dried over anhydrous magnesium sulfate, filtered and solvent was removed under reduced pressure. The residue was purified by flash column chromatography (2:1 hexanes-ethyl acetate) to provide the title compounds as an off-white powder (0.16 g., 0.538 mmol, 19.2%). $^1$HNMR (CDCl$_3$) d 7.88–6.15 (m, 12H) 3.06 (s, 3H); IR (KBr): 2922, 1602 cm$^{-1}$; Mass spec m/z 298.0 (M+H)+.

Example 201

1-Phenoxy-2-(4'-methylsulfonylphenyl)benzene

A. 2-(4'-methylthiophenyl)phenol: A mixture of 2-bromophenol (3.0 g, 17.0 mmol), 4-methylthio benzene boronic acid (3.5 g, 20.8 mmol), and tetrabutylammonium bromide (0.28 g, 0.867 mmol) in toluene (100 ml), ethanol (25 ml), and 2M sodium carbonate (50 ml) was degassed by bubbling nitrogen through for 30 minutes. Tetrakis (triphenylphosphine)palladium (0.06 g, 0.052 mmol) was added and the mixture was heated to reflux for 2.5 h. The reaction was cooled to room temperature and the layers were separated. The aqueous layer was extracted with ethyl acetate and the combined organic layers were dried, filtered, and concentrated. Purification by chromatography on silica gel using 4:1 hexane/ethyl acetate as eluant provided the desired coupled product (3.03 g., 81%) as a yellow powder; $^1$H NMR (CDCl$_3$) d 7.42 (m, 4H), 7.25 (m, 2H), 7.01 (t, 4H), 5.13 (s, 1H), 2.57 (s, 3H); Mass spectrum m/z 217 (M+H).

B. 2-(4'-nitrophenoxy)-1-(4'-methylthiophenyl)benzene: 2-(4'-Methylthiophenyl)phenol (0.4 g, 1.9 mmol) and 1-fluoro-4-nitrobenzene (0.27 g, 1.94 mmol) were dissolved in dimethylformamide (2 ml) and cooled to 0° C. Sodium hydride (80% dispersion in oil, 0.063 g, 2.1 mmol) was added and the mixture was allowed to warm to room temperature and was stirred 18 h. The reaction was diluted with ethyl acetate and water. The aqueous layer was extracted with ethyl acetate. The combined organic layers were washed with brine, dried, filtered and concentrated. Purification by chromatography on silica gel using 6:1 hexane/ethyl acetate as eluant and recrystallization (dichloromethane/hexane) afforded the product (0.59 g., 96%) as yellow crystals, mp 70–72° C.; $^1$H NMR (CDCl$_3$) d 8.11 (d, J=9.15 Hz, 2H), 7.51 (dd, 1H), 7.41–7.36 (m, 4H), 7.20 (d, J=8.42 Hz, 2H), 7.14 (dd, 1H), 6.88 (d, J=9.15 Hz, 2H), 2.46 (s, 3H); IR (KBr) 1514, 1342 cm$^{-1}$; Analysis for C$_{19}$H$_{15}$NO$_3$S: calc'd C: 67.64%, H: 4.48%, N: 4.15%; found C: 67.60%, H: 4.39%, N: 4.09%.

C. 2-phenoxy-1-(4'-methylthiophenyl)benzene: A mixture of the compound of Ex. 201, part B (0.18 g, 0.53 mmol), iron powder (0.1 g, 1.8 mmol), glacial acetic acid (0.3 ml, 5 mmol) and ethanol (10 ml) was heated to reflux for 4 h. The reaction was cooled, filtered and concentrated in vacuo. To the crude amine was added tetrahydrofuran (11 ml) and the mixture was heated. Isoamyl nitrite (0.143 ml, 1.06 mmol) was added and the reaction was heated to reflux for 4h. The reaction was concentrated and chromatographed on silica gel using hexane/ dichloromethane as eluant to afford the desired product (0.096 g., 61%) as a yellow oil; $^1$H NMR (CDCl$_3$) d 7.49 (d, J=8.42 Hz, 2H), 7.45 (dd, 1H), 7.30–7.19 (m, 6H), 7.05 (m, 2H) 6.94 (d, J=8.42 Hz, 2H), 2,48 (s, 3H), Mass spectrum m/z 293 (M+H).

D. 1-phenoxy-2-(4'-methylsulfonylphenyl)benzene: The product of Ex. 201, part C (0.096 g, 0.35 mmol) was dissolved in dichloromethane (5 ml) and cooled to 0° C. 3-Chloroperbenzoic acid (0.15 g, 0.73 mmol) was added and the mixture was stirred at room temperature for 18 h. The reaction was diluted with dichloromethane, washed successively with sodium bicarbonate, sodium bisulfite, brine and then dried, filtered and concentrated. The product was chromatographed on silica gel using 4:1 hexane/ethyl acetate as eluant and recrystallized (dichloromethane/hexane) to afford the title compound (0.063 g., 56%), mp 130–131° C. Concentration of the mother liquor provided an additional 0.02 g of product; $^1$H NMR (CDCl$_3$) d 7.94(d, J=8.79 Hz, 2H), 7.77 (d, J=8.79 Hz, 2H), 7.46 (dd, 1H), 7.37 (m, 4H), 7.09 (m, 2H), 6.94 (dd, 2H), 3.06 (s, 3H); Mass spectrum m/z 325 (M+H), 342 (M+NH$_4$); Analysis for C$_{19}$H$_{16}$O$_3$S calc'd: C: 70.35%, H: 4.97%, S: 9.88%; found C: 70.28%, H: 4.89%, S: 9.99%.

Using the above-described techniques or variations thereon appreciated by those of skill in the art of chemical synthesis, the compounds of Tables 1–3 (shown below) can also be prepared.

TABLE 1

| Ex. No. | R1X | R3 | R4 | mp °C. | Mass spec (M + H)+ |
|---|---|---|---|---|---|
| 1 | Ph | H | H | 135–137 | 326[a] |
| 2 | 4-F—Ph | H | H | 165–167 | 327 |
| 3 | 4-Me—Ph | H | H | 131–133 | 340[a] |
| 4 | 3-MeO—Ph | H | H | 121–122 | 356[a] |
| 5 | 4-MeO—Ph | H | H | 141–144 | 339 |
| 6 | 3,4-(MeO)$_2$—Ph | H | H | 161–163 | 386[a] |
| 7 | 4-Br—Ph | H | H | | |
| 8 | 3-EtO—Ph | H | H | | |
| 9 | 4-CF$_3$CH$_2$O—Ph | H | H | | |
| 10 | 4-MeOCH2O—Ph | H | H | | |
| 11 | 4-MeCOO—Ph | H | H | | |
| 12 | 4-Me$_2$NCOO—Ph | H | H | | |
| 13 | 4-PhCH$_2$COO—Ph | H | H | | |
| 14 | 4-PhCOO—Ph | H | H | | |
| 15 | 4-PhCH$_2$OOC—Ph | H | H | | |
| 16 | 4-NH$_2$—Ph | H | H | 100–103 | 324 |
| 17 | 3-Cl—Ph | H | H | | |
| 18 | 4-NO$_2$—Ph | H | H | | |
| 19 | 4-EtS—Ph | H | H | | |
| 20 | 4-Me$_2$N—Ph | H | H | 180–182 | 352 |
| 21 | 4-MeC(=O)—Ph | H | H | | |
| 22 | 4-MeC(=O)NH—Ph | H | H | | |
| 23 | 4-PhCH$_2$NH—Ph | H | H | | |
| 24 | 4-PhNH—Ph | H | H | | |
| 25 | 4-MeONH—Ph | H | H | | |
| 26 | 4-MeOOCNH—Ph | H | H | | |
| 27 | 4-PhCH$_2$OOCNH—Ph | H | H | | |
| 28 | 4-PhOOCNH—Ph | H | H | | |
| 29 | 4-MeNHCONH—Ph | H | H | | |
| 30 | 4-PhCONH—Ph | H | H | | |
| 31 | 4-PhSO$_2$NH—Ph | H | H | | |
| 32 | 4-(4-MePhSO$_2$NH)—Ph | H | H | | |
| 33 | 4-PhCH$_2$SO$_2$NH—Ph | H | H | | |
| 34 | 4-N-pyrrolidinyl-Ph | H | H | | |
| 35 | 4-N-piperidinyl-Ph | H | H | | |
| 36 | 4-N-morpholinyl-Ph | H | H | | |
| 37 | 4-(1-piperazinyl)-Ph | H | H | | |
| 38 | 4-(4-Me-1-piperazinyl)-Ph | H | H | | |
| 39 | 4-(4-benzyl-1-piperazinyl)-Ph | H | H | | |
| 40 | 4-Br—Ph | H | H | | |
| 41 | 4-CHO | H | H | 176 | 354[a] |
| 42 | 4-MeOCH2—Ph | H | H | 88 | 370[a] |
| 43 | 4-HOCH2—Ph | H | H | 134 | 356[a] |
| 44 | 4-CF$_3$—Ph | H | H | | |
| 45 | 3-pyridazinyl | H | H | | |
| 46 | 2-benzofuranyl | H | H | | |
| 47 | 5-benzothienyl | H | H | 183–185 | 382[a] |
| 48 | 2-benzothienyl | H | H | 165–167 | 382[a] |
| 49 | 2-naphthyl | H | H | 183– | 359 |

TABLE 1-continued

[Structure: MeSO$_2$-phenyl-phenyl with R$^1$X at position 2, R$^3$ at positions 5/6, R$^4$ at positions 3/4]

| Ex. No. | R1X | R3 | R4 | mp °C. | Mass spec (M + H)+ |
|---|---|---|---|---|---|
| 50 | 5-MeO-2-naphthyl | H | H | 184 202–204 | 395 |
| 51 | 3-pyridyl | H | H | 190 | 310 |
| 52 | 2-quinolyl | H | H | 148–149 | 360 |
| 53 | 3-quinolyl | H | H | 140–141 | 360 |
| 54 | 6-quinolyl | H | H | | |
| 55 | 2-thienyl | H | H | | |
| 56 | 2-thiazolyl | H | H | | |
| 57 | 3-thienyl | H | H | | |
| 58 | 2-furyl | H | H | | |
| 59 | 2-oxazolyl | H | H | | |
| 60 | N-methyl-2-pyrrolyl | H | H | | |
| 61 | 3-isoxazolyl | H | H | | |
| 62 | 3-isothiazolyl | H | H | | |
| 63 | 2-benzothiazolyl | H | H | | |
| 64 | 2-benzoxazolyl | H | H | | |
| 65 | 3-benzindazolyl | H | H | | |
| 66 | 5-benzotriazolyl | H | H | | |
| 67 | 3-benzoisothiazolyl | H | H | | |
| 68 | 3-benzoisoxazolyl | H | H | | |
| 69 | 3-isoquinolyl | H | H | | |
| 70 | 1-cyclohexenyl | H | H | 126–128 | 313 |
| 71 | cyclohexyl | H | H | 151–153 | 332[a] |
| 72 | cyclopentyl | H | H | | |
| 73 | 3-Et-cyclohexyl | H | H | | |
| 74 | 4-MeO-cyclohexyl | H | H | | |
| 75 | 2-Cl-cyclopentyl | H | H | | |
| 76 | 3-F-cyclopentyl | H | H | | |
| 77 | 2-HO-cyclohexyl | H | H | | |
| 78 | 4-F—Ph | 4-NH$_2$ | H | 168–170 | 359[a] |
| 79 | 4-F—Ph | 5-NH$_2$ | H | 157–159 | 359[a] |
| 80 | 4-F—Ph | 4-NO$_2$ | H | 170–172 | 389[a] |
| 81 | 4-F—Ph | 5-NO$_2$ | H | 214–216 | 389[a] |
| 82 | 4-F—Ph | 4-Me | H | | |
| 83 | 4-F—Ph | 4-CF$_3$ | H | | |
| 84 | 4-F—Ph | 4-Br | H | | |
| 85 | 4-F—Ph | 4-Cl | H | | |
| 86 | 4-F—Ph | 4-CN | H | | |
| 87 | Ph | 4-OH | H | 74 | 342[a] |
| 88 | 4-F—Ph | 4-OMe | 5-Cl | | |
| 89 | 4-F—Ph | 4-CH$_2$COOMe | H | | |
| 90 | 4-F—Ph | 5-CH$_2$COOMe | H | | |
| 91 | 4-F—Ph | 4-COOMe | H | | |
| 92 | 4-F—Ph | 5-COOMe | H | | |
| 93 | 4-F—Ph | 4-C(=O)Me | H | 135 | 386[a] |
| 94 | Ph | 4-SPh | H | | |
| 95 | Ph | 5-SO$_2$Me | | | |
| 96 | Ph | 4-CH=CH$_2$ | H | | |
| 97 | Ph | 4-NMe$_2$ | H | | |

TABLE 1-continued

[Structure: biphenyl with MeSO$_2$ at para position of one ring; other ring has positions 3 (R$^4$), 4, 5, 6 (R$^3$), and R$^1$X substituent]

| Ex. No. | R1X | R3 | R4 | mp °C. | Mass spec (M + H)+ |
|---|---|---|---|---|---|
| 98 | Ph | 4-SO$_2$NH$_2$ | H | | |
| 99 | Ph | 4-SO$_2$CF$_3$ | H | | |
| 100 | Ph | 4-SO$_2$CH$_2$Ph | H | | |
| 101 | Ph | 4-F | 5-F | | |
| 102 | Ph | 4-CONH$_2$ | H | | |
| 103 | 4-F—Ph | 4CH(Me)CO—OMe | H | | |
| 104 | 4-F—Ph | 4-C(=O)Ph | H | | |
| 105 | Ph | 5-CH(Me)OMe | H | | |
| 106 | Ph | 4-CH$_2$CH$_2$OPh | H | | |
| 107 | Ph | 4-CH$_2$OCOMe | H | | |
| 108 | Ph | 4-CH$_2$OCH$_2$OMe | H | | |
| 109 | Ph | H | 5-CF$_3$ | | |
| 110 | Ph | 4-CFH$_2$ | H | | |
| 111 | Ph | 4-CH$_2$OH | H | | |
| 112 | Ph | 4-CH$_2$O-cyclohexyl | H | | |
| 113 | Ph | 4-CH$_2$OCONHMe | H | | |
| 114 | Ph | 4-CH$_2$OCO—NHCH$_2$Ph | H | | |
| 115 | Ph | 4-CH$_2$OCO-(4-ClPh) | H | | |
| 116 | Ph | 4-CH$_2$OCH$_2$F | H | | |
| 117 | Ph | 4-CH$_2$O—CH$_2$OCOMe | H | | |
| 118 | Ph | 4-CH$_2$O—CH$_2$NMe$_2$ | H | | |
| 119 | Ph | 4-CH$_2$O—CH$_2$Ph | H | | |
| 120 | Ph | 4-CH$_2$O—CH$_2$COMe | H | | |
| 121 | Ph | 4-CH$_2$O—CH$_2$COOMe | H | | |
| 123 | Ph | 4-CH$_2$O—CH$_2$-2-thienyl | H | | |
| 124 | Ph | 4-CH$_2$O—CH$_2$-2-pyridyl | H | | |
| 125 | Ph | 4-CH$_2$NMe$_2$ | H | | |
| 126 | Ph | 4-CH$_2$Ph | H | | |
| 127 | Ph | 4-CH$_2$CONH$_2$ | H | | |
| 128 | Ph | 4-CH$_2$-2-thienyl | H | | |
| 129 | Ph | 4-CH$_2$-2-pyrimidyl | H | | |
| 130 | Ph | 4-CH=CHCN | H | | |
| 131 | Ph | 4-CH=CHCOMe | H | | |
| 132 | Ph | 4-CH=CHCOOH | H | | |
| 133 | Ph | 4-CH=CHNO$_2$ | H | | |
| 134 | Ph | 4-CH=CH—CH$_2$NMe$_2$ | H | | |
| 135 | (E)-4-F—C$_6$H$_5$CH=CH— | H | H | | |

TABLE 1-continued

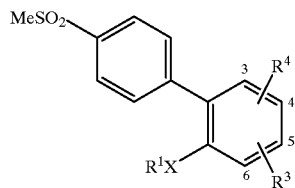

| Ex. No. | R1X | R3 | R4 | mp °C. | Mass spec (M + H)+ |
|---|---|---|---|---|---|
| 136 | 2-(4-fluorophenyl)-2-methylethyl | H | H | | |
| 137 | 4-F—C$_6$H$_5$C(CH$_3$)=CH— | H | H | | |
| 138 | phenylthio | H | H | | |
| 139 | benzylthio | H | H | | |
| 140 | C$_6$H$_5$CH(CH$_3$)S— | H | H | | |
| 141 | 4-fluorophenoxy | H | H | 126–128 | 360 |
| 142 | 4-fluorobenzoyl | H | H | | |
| 143 | cyclohexyloxy | H | H | Oil | 331 |
| 144 | phenoxy | H | H | 130–131 | 325 |
| 145 | benzyloxy | H | H | 95–97 | 339 |
| 146 | 3-pyridyloxy | H | H | | |
| 147 | C$_6$H$_5$C(=O)CH$_2$— | H | H | | |
| 148 | phenoxymethyl | H | H | | |
| 149 | phenylmethylthio | H | H | | |
| 150 | C$_6$H$_5$C(=O)CH$_2$— | H | H | | |
| 151 | 1-piperdinyl | H | H | 140–140.5 | 316 |
| 152 | C$_6$H$_5$C∫C— | H | H | 94–96 | 350$^a$ |
| 153 | 1-pyrrolyl | H | H | 133–135 | 298 |

$^a$(M + NH$_4$)+

TABLE 2

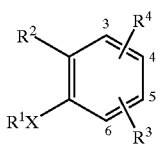

| Ex. No. | R$^1$X | R$^2$ | R$^3$ | R$^4$ | mp | Mass Spec (M + H)+ |
|---|---|---|---|---|---|---|
| 301 | 4-MePh | 5-MeSO$_2$-2-pyridyl | H | H | | |
| 302 | 4-F—Ph | 5-MeSO$_2$-2-pyridyl | H | H | | |
| 303 | Ph | 2-MeSO$_2$-5-pyridyl | H | H | 104.5–107 | 310 |
| 304 | Ph | 3-F-4-MeSO$_2$—Ph | H | H | | |
| 305 | Ph | 2-Cl-4-MeSO$_2$—Ph | H | H | | |
| 306 | Ph | 3-Me-4-MeSO$_2$Ph | H | H | | |
| 307 | Ph | 3-MeO-4-MeSO$_2$—Ph | H | H | | |
| 308 | 4-MeOPh | 5-MeSO$_2$-2-pyridyl | H | H | | |

TABLE 2-continued

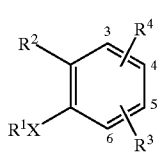

| Ex. No. | R$^1$X | R$^2$ | R$^3$ | R$^4$ | mp | Mass Spec (M + H)+ |
|---|---|---|---|---|---|---|
| 309 | 4-MeOPh | 2-MeSO$_2$-5-pyridyl | H | H | | |
| 310 | 4-MePh | 2-MeSO$_2$-5-pyridyl | H | H | | |
| 311 | 4-F—Ph | 2-MeSO$_2$-5-pyridyl | H | H | | |
| 312 | Ph | 4-H$_2$NSO$_2$—Ph | H | H | 183–184 | 310 |

TABLE 3

R²—A—R¹X

| Ex | R¹X | R² | A | mp | Mass spec (M + H)⁺ |
|---|---|---|---|---|---|
| 401 | Ph | 4-MeSO₂Ph | 2,3-naphthyl | 139–140 | 359 |
| 402 | 4-F—Ph | 4-MeSO₂Ph | 1,2-naphthyl | | |
| 403 | 4-F—Ph | 4-MeSO₂Ph | 1,2,3,4-tetrahydro-6,7-naphthyl | | |
| 404 | 4-F—Ph | 4-MeSO₂Ph | 1,2,3,4-tetrahydro-5,6-naphthyl | | |
| 405 | 4-F—Ph | 4-MeSO₂Ph | 5,6-benzothienyl | | |
| 406 | 4-F—Ph | 4-MeSO₂Ph | 1-Me-6,5-indolyl | | |
| 407 | 4-F—Ph | 4-MeSO₂Ph | 4,5-benzocycloheptyl | | |
| 408 | 4-F—Ph | 4-MeSO₂Ph | 5,6-indanyl | | |
| 409 | 4-F—Ph | 4-MeSO₂Ph | 5,6-benzimidazolyl | | |
| 410 | Ph | 4-MeSO₂Ph | 2,3-pyridyl | 126–128 | 310 |
| 411 | 4-F—Ph | 4-MeSO₂Ph | 2,3-pyridyl | 147–148 | 328 |
| 412 | 4-MeO—Ph | 4-MeSO₂Ph | 2,3-pyridyl | 138–139 | 340 |
| 413 | 4-MePh | 4-MeSO₂Ph | 2,3-pyridyl | | |

Utility

The compounds of Formula I are inhibitors of prostaglandin synthase and therefore have utility in the treatment of inflammatory diseases and as antipyretic agents. The prostaglandin G/H synthase inhibitory activity of the compounds of the present invention is demonstrated using assays of prostaglandin G/H inhibition, for example using the assay described below for assaying inhibitors of prostaglandin G/H synthase. The preferred compounds of the present invention selectively inhibit PGHS 2 activity and the production of PGE2 in human monocytes, as demonstrated using the cellular assay described below.

The compounds of Formula I have the ability to reduce pyresis in vivo, for example, as demonstrated using the animal model described below. The compounds of the present invention possess in vivo antiinflammatory activity as demonstrated using the standard animal models of acute and chronic inflammation described below. The compounds of the present-invention also have the ability to suppress/inhibit pain in vivo, as demonstrated using the animal model of analgesia described below.

As used herein "$\mu g$" denotes microgram, "mg" denotes milligram, "g" denotes gram, "$\mu L$" denotes microliter, "mL" denotes milliliter, "L" denotes liter, "nM" denotes nanomolar, "$\mu M$" denotes micromolar, "mM" denotes millimolar, "M" denotes molar and "nm" denotes nanometer. "Sigma" stands for the Sigma-Aldrich Corp. of St. Louis, Mo.

A compound is considered to be active in the prostaglandin G/H synthase inhibition assay described below if it inhibits prostaglandin G/H synthase with an $IC_{50} < 300$ $\mu M$. Selective PGHS-2 inhibitors show a ratio of $IC_{50}$ vs. PGHS-1/$IC_{50}$ vs. PGHS-2 that is >1.

Prostaglandin G/H Synthase Inhibition Assay

Prostaglandin G/H synthase (cyclooxygenase, PGHS, Cox) activity was determined spectrophotometrically essentially as described by Kulmacz et al (reference). This assay employs the reducing substrate TMPD (4,4, 4',4'-tetramethyl phenyl diamine) which upon oxidation yields an intense blue color which can be monitored at 610 nM. The assay was adapted to a 96 well microtiter dish format as described below. Test compounds were incubated with an enzyme source either, PGHS 1 or PGHS 2, in 125 $\mu L$ of buffer (40 uM Tris Maleate, 0.8% Tween 20, 1.2 $\mu M$ heme, 0.4 mg/ml gelatin, pH 6.5) for two minutes at room temperature at which time the reaction was initiated by the addition of 125 $\mu L$ of arachidonic acid in buffer (0.1M Tris/HCl. 0.2% Tween 20, pH 8.5) to give a final arachidonate concentration of 100 $\mu L$. The reaction plate was immediately placed in a microtiter reader and readings made at 610 nm for 1.5 min at 3 sec intervals. Reaction rates were calculated from the slope of the linear portion of the absorbance versus time curve. Rates for control samples lacking added inhibitors were used to calculate the percent inhibition of each test compound. Results are presented as an $IC_{50}$ value which is the concentration of added compound which causes 50% inhibition of the control rate.

Comparison of the ability to preferentially inhibit PGHS 2 versus PGHS 1 was made by a comparison Of $IC_{50}$ values obtained against the two isoforms of the enzyme. The ratio PGHS 1 $IC_{50}$/PGHS 2 $IC_{50}$ is referred to as the selectivity ratio. Compounds with a greater selectivity ratio are those compounds with greater potency toward the PGHS 2 isoform of the enzyme.

Tables A below sets forth the activity of representative compounds of the present invention in the prostaglandin G/H synthase inhibition assay described above. In table A the $IC_{50}$ values are expressed as +++=$IC_{50}$ of <10 $\mu M$, ++=$IC_{50}$ of 10–50 $\mu M$, and +=$IC_{50}$ of 50–300 $\mu M$ ($\mu M$=micromolar).

TABLE A

| Ex. No. | $IC_{50}$(PGHS 2) |
|---|---|
| 1 | ++ |
| 2 | ++ |
| 3 | ++ |
| 4 | ++ |
| 5 | +++ |
| 6 | + |
| 16 | + |
| 20 | ++ |
| 41 | ++ |
| 42 | +++ |
| 43 | + |
| 47 | ++ |
| 48 | +++ |
| 49 | ++ |
| 50 | ++ |
| 51 | + |
| 52 | + |
| 53 | + |
| 70 | ++ |
| 71 | ++ |
| 78 | + |
| 79 | + |
| 80 | ++ |
| 81 | ++ |
| 87 | + |
| 93 | ++ |
| 141 | +++ |
| 143 | +++ |
| 144 | +++ |

TABLE A-continued

| Ex. No. | IC$_{50}$(PGHS 2) |
|---|---|
| 145 | + |
| 151 | ++ |
| 152 | +++ |
| 153 | + |
| 305 | + |
| 312 | +++ |
| 401 | ++ |
| 410 | ++ |
| 411 | ++ |
| 412 | ++ |

Cellular Assay

Human peripheral blood monocytes were obtained from normal donor blood by leukophoresis and isolated by elutriation. Monocytes were suspending in RPMI medium at 2×10 6 cells/ml, and plated at 200 µL/well in 96 well microtiter plates. Test compounds were added to the cells at appropriate concentration in DMSO such that the final DMSO concentration was 0.5% in the medium. Cells and compound or DMSO alone were incubated for 1 hour at 37° C at which time cells were stimulated with 1 µg/ml LPS (Lipopolysaccharide, Salmonella typehrium, 5 mg/ml in 0.1% aqueous TEA) to induce PGHS 2 enzyme activity and prostaglandin production. Cells were incubated for 17.5 hours at 37° C. in a 95% air 5% C02 environment when culture supernates were removed to determine the extent of prostaglandin E2 (PGE2) formation by EIA (PerSeptive Diagnostics). The ability of test compounds to inhibit PGE2 production by 50% compared to DMSO treated cultures is given by the IC$_{50}$ value and represents a measure of potency against the PGHS 2 isozyme.

Table B below sets forth the activity of representative compounds of the present invention in the cellular assay described above. In table B the IC$_{50}$ values are expressed as +++=IC$_{50}$ of <10 nM, ++=IC$_{50}$ of 10–50 nM, and +=IC$_{50}$ of 51–100 nM (nM=nanomolar).

TABLE B

| Ex. No. | IC$_{50}$ (PGE2) |
|---|---|
| 2 | ++ |
| 4 | + |
| 5 | ++ |
| 20 | ++ |
| 41 | + |
| 48 | ++ |
| 49 | + |
| 81 | + |
| 144 | + |

Rat Antipyrexia Test

The antipyretic activity of test compounds was determined by the method described by Smith and Hambourger (J. Pharmacol. Exp. Ther., 54, 346–351, (1935)). Male rats are equilibrated in test room for 7 hours on day 1 at which time food is removed and rats are dosed (s.c) with a 20% solution of Schiff's brewer's yeast (in saline) to induce fever. A control group receiving saline alone is also maintained. On day 2 beginning 19 hours post-dosing rat temperatures are taken and animals are dosed either P.O., S.C., I.P, or I.V. with the appropriate doses of test compound or vehicle. Temperatures are recorded each hour thereafter for six hours. Pyresis is defined as the change in mean rectal temperature between control and yeast-injected animals. Antipyretic activity reflects the extent of mean rectal temperature lowering produced by test compounds in those animals dosed with compound versus those receiving vehicle alone. An ED50 value is calculated as the dose of compound required to decrease pyresis by 50%.

The compounds of the present invention were tested in the above Rat Antipyrexia Test and had ED50 values of ≦30mg/kg.

Rat Carrageenan Paw Edema Test

Antiinflammatory activity of test compounds was determined by the method of Winter, C. A., Risley, E. A., and Nuss, G. W. (Proc. Soc. Exp. Biol. Med., 111, 544–547 (1962)) and briefly presented as follows. Male Lewis rats receive an injection of 0.1 ml of 1% carrageenan (in saline) into the plantar tissue of one hind paw. Control rats are injected with saline alone. Three hours later, paw swelling is determined as a measure of the inflammatory response. Animals are administered test compounds or vehicle either P.O., S.C., I.P., or I.V. one hour prior to footpad injection. The decrease in hind paw swelling produced by test compounds versus vehicle controls represents a measure of antiinflammatory activity. An ED30 value is calculated as the dose of compound required to decrease the magnitude of paw swelling by 30%.

Rat Adjuvant Arthritis Test

Antiinflammatory activity was evaluated according to the method described by Pearson, C. M. (Proc. Soc. Exp. Biol. Med., 91, 95–101 (1956)). Briefly, male Lewis rats received an injection of complete Freunds' adjuvant (0.1 ml of 5 mg/ml in light mineral oil) or mineral oil alone (0.1 ml) into a hind footpad. On day 18 post-injection, joint swelling is determined compared to a mineral oil injected control as a measure of inflammation. Animals are administered compounds or vehicle either P.O., S.C., I.P., or I.V. from day 0 to day 18. The decrease in joint swelling in dosed animals versus vehicle controls is a measure of antiinflammatory activity. An ED50 value is calculated as the dose of compound required to decrease the magnitude of joint swelling by 50% compared to controls.

Rat Randall Selitto Test

Analgesic activity was evaluated in the rat inflamed yeast-paw test modified from the method of Randall, L. O. and Selitto, J. J. (Arch. Int. Pharmacodyn. Ther. 3, 409–419 (1957)) employing an Ugo Basile analgesiometer (Stoelting). Fasted male rats were screened on both hind paws for preyeast threshold pain response (vocalization or struggle) of less than 15 cm slide travel on the analgesiometer. The right hind paw was then inflamed by a subplantar injection (0.1 ml) of a 20% aqueous suspension of Fleischmann's active dry yeast. Compounds were dosed P.O., S.C., I.P., or I.V. 2 hours after the yeast injection. Pain reaction thresholds were determined 0.5, 1, 2, and 4 hours later. An ED$_{30}$ value is calculated as the dose of compound required to increase the pain threshold by 30% compared to controls.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release Formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed as an antiinflammatory or antipyretic agent.

The compounds of this invention can be administered by any means that produces contact of the active agent with the agent's site of action, PGHS-2, in the body of a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. For a normal male adult human of approximately 70 kg of body weight, this translates into a dosage of 70 to 1400 mg/day. Intravenously, the most preferred doses will range from about 1 to about 10 mg/kg/minute during a constant rate infusion. Advantageously, compounds of the present invention may be administered in a single daily dose, or the total daily dosage may be administered in divided doses of two, three, or four times daily.

The compounds of the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions. It can also be administered parenterally, in sterile liquid dosage forms.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours.

Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remingtons Pharmaceutical Sciences, Mack Publishing Company, a standard reference text in this field. Useful pharmaceutical dosage-forms for administration of the compounds of this invention can be illustrated as follows:

Capsules

Capsules are prepared by conventional procedures so that the dosage unit is 500 milligrams of active ingredient, 100 milligrams of cellulose and 10 milligrams of magnesium stearate.

A large number of unit capsules may also be prepared by filling standard two-piece hard gelatin capsules each with 100 milligrams of powdered active ingredient, 150 milligrams of lactose, 50 milligrams of cellulose, and 6 milligrams magnesium stearate.

Syrup

| Wt. % | |
|---|---|
| Active Ingredient | 10 |
| Liquid Sugar | 50 |
| Sorbitol | 20 |
| Glycerine | 5 |
| Flavor, Colorant and Preservative as required | |
| Water as required | |

The final volume is brought up to 100% by the addition of distilled water.

Aqueous Suspension

| Wt. % | |
|---|---|
| Active Ingredient | 10 |
| Sodium Saccharin | 0.01 |
| Keltrol ® (Food Grade Xanthan Gum) | 0.2 |
| Liquid Sugar | 5 |
| Flavor, Colorant and Preservative as required | |
| Water as required | |

Xanthan gum is slowly added into distilled water before adding the active ingredient and the rest of the Formulation ingredients. The final suspension is passed through a homogenizer to assure the elegance of the final products.

Resuspendable Powder

| Wt. % | |
|---|---|
| Active Ingredient | 50.0 |
| Lactose | 35.0 |
| Sugar | 10.0 |
| Acacia | 4.7 |
| Sodium Carboxylmethylcellulose | 0.3 |

Each ingredient is finely pulverized and then uniformly mixed together. Alternatively, the powder can be prepared as a suspension and then spray dried.

| Semi-Solid Gel Wt. % | |
|---|---|
| Active Ingredient | 10 |
| Sodium Saccharin | 0.02 |
| Gelatin | 2 |
| Flavor, Colorant and preservative as required | |
| Water as required | |

Gelatin is prepared in hot water. The finely pulverized active ingredient is suspended in the gelatin solution and then the rest of the ingredients are mixed in. The suspension is filled into a suitable packaging container and cooled down to form the gel.

Semi-Solid Paste

| Wt. % | |
|---|---|
| Active Ingredient | 10 |
| Gelcarin ® (Carrageenin gum) | 1 |
| Sodium Saccharin | 0.01 |
| Gelatin | 2 |
| Flavor, Colorant and Preservative as required | |
| Water as required | |

Gelcarin® is dissolved in hot water (around 80° C.) and then the fine-powder active ingredient is suspended in this solution. Sodium saccharin and the rest of the Formulation ingredients are added to the suspension while it is still warm. The suspension is homogenized and then filled into suitable containers.

Emulsifiable Paste

| Wt. % | |
|---|---|
| Active Ingredient | 30 |
| Tween ® 80 and Span ® 80 | 6 |
| Keltrol ® | 0.5 |
| Mineral Oil | 63.5 |

All the ingredients are carefully mixed together to make a homogenous paste.

Soft Gelatin Capsules

A mixture of active ingredient in a digestable oil such as soybean oil, cottonseed oil or olive oil is prepared and injected by means of a positive displacement pump into gelatin to form soft gelatin capsules containing 100 milligrams of the active ingredient. The capsules are washed and dried.

Tablets

Tablets may be prepared by conventional procedures so that the dosage unit is 500 milligrams of active ingredient, 150 milligrams of lactose, 50 milligrams of cellulose and 10 milligrams of magnesium stearate.

A large number of tablets may also be prepared by conventional procedures so that the dosage unit was 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Injectable

A parenteral composition suitable for administration by injection is prepared by stirring 1.5% by weight of active ingredient in 10% by volume propylene glycol and water. The solution is made isotonic with sodium chloride and sterilized.

Suspension

An aqueous suspension is prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

The compounds of the present invention may be administered in combination with a second therapeutic agent. The compound of Formula I and such second therapeutic agent can be administered separately or as a physical combination in a single dosage unit, in any dosage form and by various routes of administration, as described above.

The compound of Formula I may be Formulated together with the second therapeutic agent in a single dosage unit (that is, combined together in one capsule, tablet, powder, or liquid, etc.). When the compound of Formula I and the second therapeutic agent are not E7 Formulated together in a single dosage unit, the compound of Formula I and the second therapeutic agent may be administered essentially at the same time, or in any order; for example the compound of Formula I may be administered first, followed by administration of the second agent. When not administered at the same time, preferably the administration of the compound of Formula I and the second therapeutic agent occurs less than about one hour apart, more preferably less than about 5 to 30 minutes apart.

Preferably the route of administration of the compound of Formula I is oral. Although it is preferable that the compound of Formula I and the second therapeutic agent are both administered by the same route (that is, for example, both orally), if desired, they may each be administered by different routes and in different dosage forms (that is, for example, one component of the combination product may be administered orally, and another component may be administered intravenously). The dosage of the compound of Formula I when administered alone or in combination with a second therapeutic agent may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired, as described above. Particularly when provided as a single dosage unit, the potential exists for a chemical interaction between the combined active ingredients. For this reason, when the compound of Formula I and a second therapeutic agent are combined in a single dosage unit they are Formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a sustained-release material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the Formulation of a combination product in which the one component is coated with a sustained and/or enteric release polymer, and the other component is also coated with a polymer such as a lowviscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The present invention also includes pharmaceutical kits useful, for example, in the treatment or prevention of inflammatory diseases, which comprise one or more containers containing a pharmaceutical composition comprising a therapeutically effective amount of a compound of Formula I. Such kits may further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, may also be included in the kit.

In the present disclosure it should be understood that the specified materials and conditions are important in practicing the invention but that unspecified materials and conditions are not excluded so long as they do not prevent the benefits of the invention from being realized.

The term "consisting essentially of" where used in the present disclosure is intended to have its customary meaning; namely, that all specified materials and conditions are very important in practicing the invention but that unspecified materials and conditions are not excluded so long as they do not prevent the benefits of the invention from being realized.

The foregoing disclosure includes all the information deemed essential to enable those of skill in the art to practice the claimed invention. Because the cited references may provide further useful information, however, these cited materials are hereby incorporated by reference.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of Formula I:

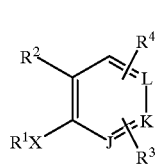

(I)

or a pharmaceutically acceptable salt or prodrug form thereof, wherein:

J, K, and L are independently $CR^3$, $CR^4$ or N;

X is a single bond, (i.e. X is absent), —$(CHR^5)_2$—, —CH=$CR^5$—, —$CR^5$=CH—, —C∫C—, —$(CHR^5)_pZ$—, —$Z(CHR^5)_p$—, —C(=O)$CH_2$, or —$CH_2C$(=O)—;

Z is O or S;

R¹ is:
  phenyl substituted with 0–2 R⁷,
  2-naphthyl substituted with 0–2 R⁷,
  $C_5$–$C_7$ cycloalkyl substituted with 0–1 R⁹,
  $C_5$–$C_7$ cycloalkenyl, provided that when R¹ is attached directly to a heteroatom, said heteroatom is not attached to a carbon bearing a double bond in the cycloalkene ring,.
  a 5- to 10-membered heterocyclic ring system selected from furyl, thienyl, pyrrolyl, thiazolyl, oxazolyl, N-methylpyrrolyl, isoxazolyl, isothiazolyl, pyrazolyl, 3-pyridinyl, pyridazinyl, pyrazinyl, indolyl, benzofuranyl, benzothienyl, benzothiazolyl, benzoxazolyl, benzotriazolyl, benzoisothiazolyl, benzisoxazolyl, quinolinyl, isoquinolinyl, or piperidinyl, said heterocyclic ring system being substituted with 0–2 R⁷;

R² is:

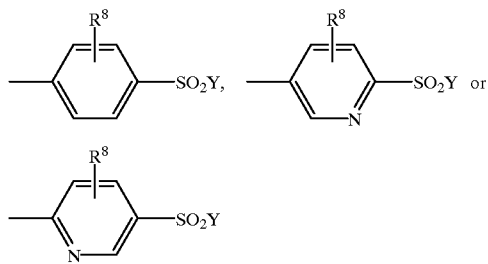

Y is —$CH_3$ or $NH_2$;

R³ is: H, F, Br, Cl, I, CN, $C_1$–$C_4$ alkyl substituted with 0–1 R¹², $C_1$–$C_4$ haloalkyl, $C_1$–$C_4$ alkenyl substituted with 0–1 R¹³, $NO_2$, $NR^{15}R^{16}$, $S(O)_mR^{11}$, $SO_2NR^{15a}R^{16}$, —C(=O)R⁶, —COOR¹⁷, C(=O)NR^{15a}R^{16}, or OR¹⁸;

R⁴ is H, F, Br, Cl, I, $C_1$–$C_2$ alkyl, $C_1$–$C_2$ alkoxy, $C_1$–$C_2$ haloalkyl, —$CH_3$, —$SR^{10a}$,
alternately, when R³ and R⁴ are substituents on adjacent carbon atoms, R³ and R⁴ can be taken together with the carbon atoms to which they are attached to form a 5–7 membered carbocyclic or heterocyclic ring system, said heterocyclic ring system containing from 1–3 heteroatoms selected from N, O or S;

R⁵ is $C_1$–$C_2$ alkyl, $C_1$–$C_2$ alkoxy, or $C_1$–$C_2$ haloalkyl;

R⁶ is
  hydrogen,
  $C_1$–$C_6$ alkyl substituted with 0–1 R¹⁴,
  phenyl substituted with 0–2 R⁹,
  $C_5$–$C_7$ cycloalkyl substituted with 0–1 R⁹,
  a 5- to 10-membered heterocyclic ring system selected from furyl, thienyl, thiazolyl, oxazolyl, N-methylpyrrolyl, isoxazolyl, isothiazolyl, pyrazolyl, pyridinyl, pyridazinyl, pyrazinyl, or pyrimidinyl, said heterocyclic ring system being substituted with 0–2 R⁷;

R⁷ is a substituent on carbon that is selected from: H, F, Br, Cl, I, $C_1$–$C_4$ alkyl, phenyl, $CH_2OH$, $CH_2OCH_3$, $C_1$–$C_4$ alkoxy, $C_1$–$C_4$ haloalkyl, —SR¹⁰, $NR^{15}R^{16}$, —C(=O)R¹⁰, $CH_2COOR^{17}$, or OR¹⁹; provided that when X is a single bond then R⁷ is not ortho to X.

R⁸ is H, F. Br, Cl, I, hydroxy, $C_1$–$C_4$ alkyl, $C_1$–$C_4$ alkoxy, —(CH_2)_nCOOR¹⁷, or —CH=CHCOOR¹⁷;

R⁹ is H, F, Br, Cl, I, hydroxy, $C_1$–$C_4$ alkyl, or $C_1$–$C_4$ alkoxy;

R¹⁰ is H or $C_1$–$C_4$ alkyl;

R^{10a} is $C_1$–$C_4$ alkyl;

R¹¹ is $C_1$–$C_4$ alkyl, $C_1$–$C_2$ fluoroalkyl, phenyl, or benzyl;

R¹² is F, OR¹⁸, $NR^{15}R^{16}$, phenyl substituted with 0–2 R⁹, —CN, —C(=O)R⁶, —COOR¹⁷, —C(=O)NR^{15}R^{16}, or
a heterocyclic ring system selected from morpholinyl, piperidinyl, pyrrolidinyl, furyl, thienyl, pyridinyl, piperidazinyl, pyrimidinyl, pyrazinyl, or tetrahydropyridinyl, said heterocyclic ring system being substituted with 0–2 R⁹;

R¹³ is —CN, —C(=O)R⁶, —COOR¹⁷, —$NO_2$, or $NR^{15}R^{16}$;

R¹⁴ is F, OH, $C_1$–$C_4$ alkoxy, $NH_2$, phenyl substituted with 0–2 R⁹, alkylcarbonyl, arylcarbonyl, —COOR¹⁷, or —C(=O)$NH_2$;

R¹⁵ is H, $C_1$–$C_4$ alkyl substituted with 0–1 R²³, $C_6$–$C_{10}$ aryl, $C_3$–$C_7$ cycloalkyl, $C_4$–$C_{11}$ cycloalkylalkyl, $C_2$–$C_4$ alkenyl, $C_1$–$C_4$ alkoxy, $C_1$–$C_6$ alkylcarbonyl, $C_1$–$C_6$ alkoxycarbonyl, $C_7$–$C_{14}$ arylalkoxycarbonyl, $C_6$–$C_{10}$ aryloxycarbonyl, $C_1$–$C_6$ alkylaminocarbonyl, $C_6$–$C_{10}$ arylcarbonyl, $C_1$–$C_6$ alkylsulfonyl, $C_6$–$C_{10}$ arylsulfonyl, $C_7$–$C_{14}$ alkylarylsulfonyl, $C_7$–$C_{14}$ aralkylsulfonyl;

R^{15a} is H, $C_1$–$C_4$ alkyl substituted with 0–1 R²³, $C_6$–$C_{10}$ aryl, $C_3$–$C_7$ cycloalkyl, $C_4$–$C_{11}$ cycloalkylalkyl, $C_2$–$C_4$ alkenyl, $C_1$–$C_4$ alkoxy;

R¹⁶ is H, or $C_1$–$C_4$ alkyl;
alternately, R¹⁵ and R¹⁶ can be taken together to be —(CH_2)_4—, —(CH_2)_5—, —(CH_2)_2O(CH_2)_2—, or —(CH_2)_2NR^{21}(CH_2)_2—, R¹⁷ is $C_1$–$C_4$ alkyl, or arylalkyl;

R¹⁸ is $C_1$–$C_4$ alkyl substituted with 0–2 R²⁴, $C_6$–$C_{10}$ aryl, $C_3$–$C_7$ cycloalkyl, $C_1$–$C_6$ alkylcarbonyl, $C_1$–$C_6$ alkylaminocarbonyl, $C_7$–$C_{14}$ arylalkylcarbonyl, or $C_6$–$C_{10}$ arylcarbonyl substituted with 0–2 R⁹;

R¹⁹ is $C_1$–$C_4$ alkyl, $C_1$–$C_4$ haloalkyl, $C_1$–$C_4$ alkoxyalkyl, $C_1$–$C_6$ alkylcarbonyl, $C_1$–$C_6$ alkylaminocarbonyl, $C_7$–$C_{14}$ arylalkylcarbonyl, or $C_6$–$C_{10}$ arylcarbonyl substituted with 0–2 R⁹;

R²⁰ is H, $C_1$–$C_4$ alkyl, $C_1$–$C_4$ haloalkyl, $C_1$–$C_4$ alkoxyalkyl, $C_6$–$C_{10}$ aryl, $C_3$–$C_7$ cycloalkyl, $C_1$–$C_6$ alkylcarbonyl, $C_1$–$C_6$ alkylaminocarbonyl, $C_7$–$C_{14}$ arylalkylcarbonyl, or $C_6$–$C_{10}$ arylcarbonyl substituted with 0–2 R⁹;

R²¹ is $C_1$–$C_4$ alkyl or benzyl;

R²² is H, R², R¹, $C_1$–$C_4$ alkyl, $C_4$–$C_{10}$ cycloalkylalkyl, $C_7$–$C_{14}$ arylalkyl, or $C_6$–$C_{10}$ heteroarylalkyl;

R²³ is H, F, phenyl substituted with 0–2 R⁹, —C(=O)R⁶, —COOR¹⁷, —C(=O)NHR¹⁶, or
a heterocyclic ring system selected from morpholinyl, piperidinyl, pyrrolidinyl, furyl, thienyl, or tetrahydropyridinyl, said heterocyclic ring system being substituted with 0–2 R⁹;

R²⁴ is H, F, $NR^{15}R^{16}$, phenyl substituted with 0–2 R⁹, $C_1$–$C_4$ alkoxy, $C_1$–$C_4$ alkylcarbonyloxy, C(=O)R⁶, —COOR¹⁷, —C(=O)NR^{15}R^{16,}, or
a heterocyclic ring system selected from morpholinyl, piperidinyl, pyrrolidinyl, furyl, thienyl, piperidinyl, or tetrahydropyridinyl, said heterocyclic ring system being substituted with 0–2 R⁹;

m is 0–2; and p is 0–1;

provided that:

when J and L are both nitrogen and K is $CR^4$, then $R^4$ cannot be $SR^{10}$;

when $R^3$ and $R^4$ are taken together to form a 6 membered carbocyclic ring system and $R^1X$ is phenyl, $R^2$ is not 4-methylsulfonylphenyl;

when J is nitrogen and $R^3$ and $R^4$ are hydrogen and $R^1X$ is phenyl, $R^2$ is not 4-methylsulfonylphenyl;

when $R^3$ and $R^4$ are hydrogen and $R^1X$ is phenyl, $R^2$ is not 4-aminosulfonylphenyl.

2. A compound of claim 1 or a pharmaceutically acceptable salt or prodrug form thereof, wherein:

J is CH or N;

Each of K and L independently is $CR^3$ or $CR^4$;

X is a single bond, (i.e. X is absent), —C∫C—, or —$(CHR^5)_pZ$—;

$R^3$ is: H, F, Br, CN, $C_1$–$C_4$ alkyl substituted with 0–1 $R^{12}$, $C_1$–$C_4$ haloalkyl, $NO_2$, $SO_mR^{11}$, —C(=O)$R^6$, or $OR^{18}$;

$R^4$ is H, F, $CH_3$, or alternately, when $R^3$ and $R^4$ are substituents on adjacent carbon atoms, $R^3$ and $R^4$ can be taken together with the carbon atoms to which they are attached to form a 5–7 membered carbocyclic ring system;

$R^6$ is hydrogen, $C_1$–$C_6$ alkyl substituted with 0–1 $R^{14}$, or phenyl substituted with 0–2 $R^9$;

$R^7$ is a substituent on carbon that is selected from: H, F, Br, $C_1$–$C_4$ alkyl, $CH_2OH$, $CH_2OCH_3$, $C_1$–$C_4$ alkoxy, $C_1$–$C_4$ haloalkyl, $NR^{15}R^{16}$, or —C(=O)$R^{10}$;

where all other substituents for Formula I are as defined herein above;

provided that:

when $R^3$ and $R^4$ are taken together to form a 6 membered carbocyclic ring system and $R^1X$ is phenyl, $R^2$ is not 4-methylsulfonylphenyl;

when J is nitrogen and $R^3$ and $R^4$ are hydrogen and $R^1X$ is phenyl, $R^2$ is not 4-methylsulfonylphenyl;

when $R^3$ and $R^4$ are hydrogen and $R^1X$ is phenyl, $R^2$ is not 4-aminosulfonylphenyl.

3. A compound of claim 2 or a pharmaceutically acceptable salt or prodrug form thereof, wherein:

$R^8$ is H;

$R^9$ is H;

$R^{12}$ is F, $OR^{18}$, CN, —$COOR^{17}$;

$R^{14}$ is H;

$R^{15}$ is H, or $C_1$–$C_4$ alkyl;

$R^{16}$ is H or $C_1$–$C_4$ alkyl;

$R^{18}$ is H or $C_1$–$C_4$ alkyl;

$R^{19}$ is $C_1$–$C_4$ alkyl.

provided that:

when $R^3$ and $R^4$ are taken together to form a 6 membered carbocyclic ring system and $R^1X$ is phenyl, $R^2$ is not 4-methylsulfonylphenyl;

when J is nitrogen and $R^3$ and $R^4$ are hydrogen and $R^1X$ is phenyl, $R^2$ is not 4-methylsulfonylphenyl;

when $R^3$ and $R^4$ are hydrogen and $R^1X$ is phenyl, $R^2$ is not 4-aminosulfonylphenyl.

4. A compound of claim 1 of Formula Ia:

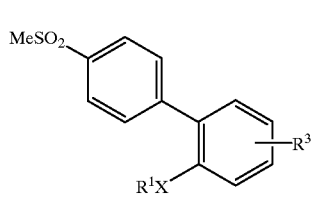

(Ia)

wherein:

$R^1X$ is phenyl, 4-fluorophenyl, 3-methoxyphenyl, 4-methoxyphenyl, 3,4-dimethoxyphenyl, 4-hydroxymethylphenyl, 4-methoxymethylphenyl, 4-dimethylaminophenyl, 4-formylphenyl, 2-naphthyl, 5-methoxy-2-naphthyl, 2-quinolinyl, 3-quinolinyl, 2-benzothienyl, 5-benzothienyl, 3-pyridyl, phenylacetylenyl, phenoxy, cyclohexenyl, cyclohexyl, 4-fluorophenoxy, cyclohexyloxy, benzyloxy, 1-pyrrolyl or 1-piperidinyl; and $R^3$ is hydrogen, 4-hydroxy, 4-nitro, 5-nitro or 4-aceto.

5. A compound of claim 4 or a pharmaceutically acceptable salt or prodrug form thereof, wherein:

$R^1X$ is phenyl; and $R^3$ is hydrogen, 4-hydroxy, 4-nitro, 5-nitro or 4-aceto; or $R^1X$ is 4-fluorophenyl, 3-methoxyphenyl, 4-methoxyphenyl, 3,4-dimethoxyphenyl, 4-hydroxymethylphenyl, 4-methoxymethylphenyl, 4-dimethylaminophenyl, 4-formylphenyl, 2-naphthyl, 5-methoxy-2-naphthyl, 2-quinolinyl, 3-quinolinyl, 2-benzothienyl, 5-benzothienyl, 3-pyridyl, phenylacetylenyl, phenoxy, cyclohexenyl, cyclohexyl, 4-fluorophenoxy, cyclohexyloxy, benzyloxy, 1-pyrrolyl or 1-piperdinyl; and $R^3$ is hydrogen.

6. The compounds which are:

(a) 2-(4'-methylsulfonylphenyl)-1-biphenyl, (b) 2-(4'-methylsulfonylphenyl)-1-(4'-flourophenyl)-benzene, (c) 2-(4'-methylsulfonylphenyl)-1-(4'-methylphenyl)-benzene, (d) 2-(4'-methylsulfonylphenyl)-1-(3'-methoxyphenyl)

(e) 2-(4'-methylsulfonylphenyl)-1-(4'-methoxyphenyl)-benzene, (f) 2-(4'-methylsulfonylphenyl)-1-(3',4'-methoxyphenyl)-benzene, (g) 2-(4'-methylsulfonylphenyl)-1-(4'-aminophenyl)-benzene, (h) 2-(4'-methylsulfonylphenyl)-1-(4'-dimethylaminophenyl)-benzene, (i) 2-(4'-methylsulfonylphenyl)-1-(4'-benzaldehyde)-benzene, (j) 2-(4'-methylsulfonylphenyl)-1-(4'-methoxymethylphenyl)-benzene, (k) 2-(4'-methylsulfonylphenyl)-1-(4'-hydroxymethylphenyl)-benzene, (l) 2-(4'-methylsulfonylphenyl)-1-(5-benzothienyl)-benzene, (m) 2-(4'-methylsulfonylphenyl)-1-(2-benzothienyl)-benzene, (n) 2-(4'-methylsulfonylphenyl)-1-(2-naphthyl)-benzene, (o) 2-(4'-methylsulfonylphenyl)-1-(5'-methoxy-2-naphthyl)-benzene, (p) 2-(4'-methylsulfonylphenyl)-1-(3-pyridyl)-benzene,
(q) 2-(4'-methylsulfonylphenyl)-1-(2-quinolyl)-benzene,
(r) 2-(4'-methylsulfonylphenyl)-1-(3-quinolyl)-benzene,
(s) 2-(4'-methylsulfonylphenyl)-1-(cyclohexenyl)-benzene,
(t) 2-(4'-methylsulfonylphenyl)-1-(cyclohexyl)-benzene,
(u) 2-(4'-methylsulfonylphenyl)-1-(4'-fluorophenyl)-(4'-amino)-benzene,
(v) 2-(4'-methylsulfonylphenyl)-1-(4'-fluorophenyl)-(5'-amino)-benzene,
(w) 2-(4'-methylsulfonylphenyl)-1-(4'-fluorophenyl)-(4'-nitro)-benzene,
(x) 2-(4'-methylsulfonylphenyl)-1-(4'-fluorophenyl)-(5'-nitro)-benzene,
(y) 2-(4'-methylsulfonylphenyl)-1-(4'-fluorophenyl)-(4'-trifluromethyl)-benzene,
(z) 2-(4'-methylsulfonylphenyl)-1-(4'-fluorophenyl)-4-bromobenzene,
(aa) 2-(4'-methylsulfonylphenyl)-1-(4'-fluorophenyl)-4-chlorobenzene,
(bb) 2-(4'-methylsulfonylphenyl)-1-(4'-fluorophenyl)-4-acetylbenzene,
(cc) 2-(4'-methylsulfonylphenyl)-1-(4'-fluorophenoxy)-benzene,
(dd) 2-(4'-methylsulfonylphenyl)-1-(cyclohexyloxy)-benzene,
(ee) 2-(4'-methylsulfonylphenyl)-1-(phenoxy)-benzene,
(ff) 2-(4'-methylsulfonylphenyl)-1-(benzyloxy)-benzene,
(gg) 2-(4'-methylsulfonylphenyl)-1-(piperidinyl)-benzene,
(hh) 2-(4'-methylsulfonylphenyl)-1-(phenylacetylene)-benzene,
(ii) 2-(4'-methylsulfonylphenyl)-1-(pyrrolyl)-benzene,
(jj) 2-(5-methylsulfonyl-2-pyridyl)-1-(4'-methylphenyl)-benzene,
(kk) 2-(5-methylsulfonyl-2-pyridyl)-1-(4'-fluorophenyl)-benzene,
(ll) 2-(2-methylsulfonyl-2-pyridyl)-1-biphenyl,
(mm) 3-(4'-methylsulfonylphenyl)-2-(4'-fluorophenyl)-pyridine
(nn) 3-(4'-methylsulfonylphenyl)-2-(4'-methoxyphenyl)-pyridine
(oo) 3-(4'-methylsulfonylphenyl)-2-(4'-methylphenyl)-pyridine.

7. The compound 3-(4'-methylsulfonylphenyl)-2-(4'-methoxyphenyl)-pyridine, or a pharmaceutically acceptable salt or prodrug form thereof.

8. A pharmaceutical composition comprising a therapeutically effective amount of a compound of claim 7 and a pharmaceutically effective carrier.

9. A method for the treatment of prostaglandin synthase disorders which comprises administering to a host in need of such treatment a therapeutically effective amount of a compound of claim 7.

\* \* \* \* \*